United States Patent [19]

Yamane et al.

[11] Patent Number: 4,690,919
[45] Date of Patent: Sep. 1, 1987

[54] BENZOXAZINORIFAMYCIN DERIVATIVE, PROCESS FOR PREPARING THE SAME AND ANTIBACTERIAL AGENT CONTAINING THE SAME

[75] Inventors: Takehiko Yamane, Akashi; Takuji Hashizume, Takasago; Katsuji Yamashita, Kobe; Kiyoshi Watanabe, Akashi, all of Japan

[73] Assignee: Kanegafuchi Kagaku Kogyo Kabushiki Kaisha, Osaka, Japan

[21] Appl. No.: 826,398

[22] Filed: Feb. 5, 1986

[30] Foreign Application Priority Data

Feb. 5, 1985 [JP] Japan .................................. 60-20384

[51] Int. Cl.⁴ .................. C07D 498/18; A61K 31/535
[52] U.S. Cl. ..................................... 514/183; 540/457
[58] Field of Search .......................... 540/457; 514/183

[56] References Cited

U.S. PATENT DOCUMENTS 3,338,888 8/1967 Bickel et al. ......................... 540/457

FOREIGN PATENT DOCUMENTS 231092 12/1984 Japan .................................. 540/457

OTHER PUBLICATIONS

Noller, "Chemistry of Organic Compounds", 2nd Edition, (1957), (Saunders), p. 170.

Primary Examiner—Robert T. Bond

Attorney, Agent, or Firm—Armstrong, Nikaido, Marmelstein & Kubovcik

[57] ABSTRACT

A novel rifamycin derivative having the general formula (I):

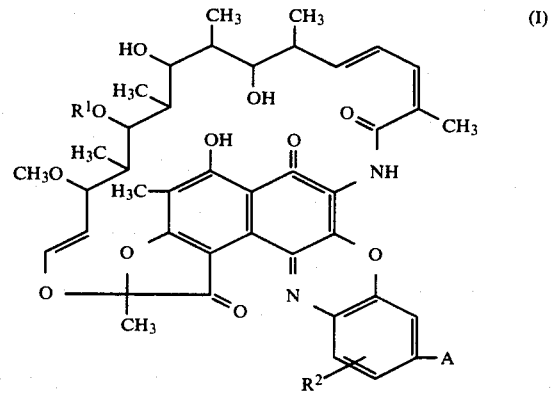

or salts thereof, a process for preparing the same and antibacterial agents containing the same as an effective component.

The rifamycin derivative of the present invention having the general formula (I) shows a strong antibacterial activity against the Gram-positive bacteria and the acid-fast bacteria.

30 Claims, No Drawings

BENZOXAZINORIFAMYCIN DERIVATIVE, PROCESS FOR PREPARING THE SAME AND ANTIBACTERIAL AGENT CONTAINING THE SAME

BACKGROUND OF THE INVENTION

The present invention relates to a novel rifamycin derivative or salts thereof, a process for preparing the same and antibacterial agents containing the same as an effective component. More particularly, the present invention relates to a novel rifamycin derivative having the general formula (I):

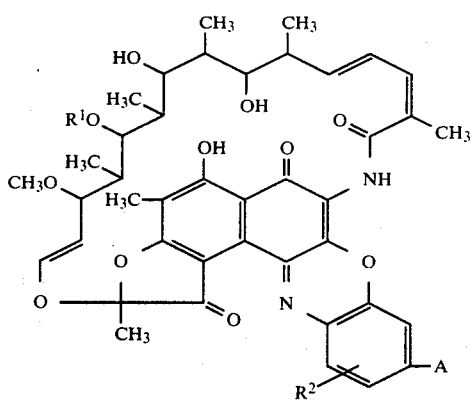

wherein $R^1$ is hydrogen atom or acetyl group; $R^2$ is hydrogen atom or hydroxyl group; A is a group represented by the formula:

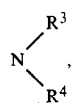

wherein $R^3$ is an alkyl group with 1 to 5 carbon atoms or an alkoxyalkyl group with 2 to 6 carbon atoms and $R^4$ is an alkyl group with 1 to 5 carbon atoms, a group represented by the formula: $-(CH^2)_aX^1$, wherein a is 1 to 4 and $X^1$ is ethynyl group, cyano group, a group having the formula:

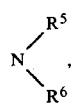

wherein $R^5$ and $R^6$ are the same or different from each other and are hydrogen atom or an alkyl group with 1 to 3 carbon atoms, a group represented by the formula: $OR^7$, wherein $R^7$ is hydrogen atom or an alkyl group with 1 to 4 carbon atoms, a group represented by the formula:

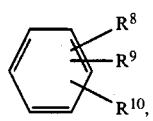

wherein $R^8$, $R^9$ and $R^{10}$ are the same or different from each other and are hydrogen atom or an alkoxy group with 1 to 3 carbon atoms, or a group represented by the formula;

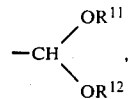

wherein $R^{11}$ and $R^{12}$ are the same or different from each other and are an alkyl group with 1 to 3 carbon atoms; a cycloalkyl group with 3 to 8 carbon atoms, a group represented by the formula:

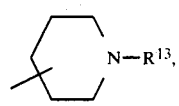

wherein $R^{13}$ is hydrogen atom or an alkyl group with 1 to 3 carbon atoms, or a group represented by the formula: $-CH_2(CHOH)_4CH_2OH$; a group represented by the formula:

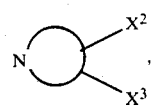

wherein

is a 3 to 10 memebered cyclic amino group with 2 to 9 carbon atoms, $X^2$ is hydrogen atom or an alkyl group having 1 to 4 carbon atoms and $X^3$ is hydrogen atom, an alkyl group with 1 to 3 carbon atoms, hydroxyl group, a group represented by the formula:

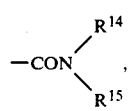

wherein $R^{14}$ and $R^{15}$ are the same or different from each other and are hydrogen atom or an alkyl group with 1 to 4 carbon atoms, a hydroxyalkyl group with 1 to 3 carbon atoms or cyclic or noncyclic amino group with 2 to 6 carbon atoms, or $X^2$ and $X^3$ when taken together represent=O group or the group represented by the formula: $-O(CH_2)_bO-$, wherein b is 2 to 4, a group represented by the formula:

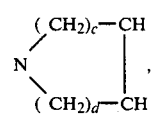

wherein c and d are the same or different from each other and are 1 to 4, a group represented by the formula:

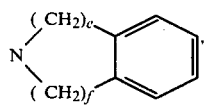

wherein e and f are the same or different from each other and are 1 to 4, or a group represented by the formula:

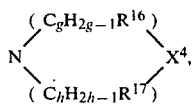

wherein g and h are the same or different from each other and are 1 to 4, $R^{16}$ and $R^7$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group with 1 to 3 carbon atoms, a phenyl group represented by the formula:

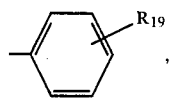

wherein $R^{19}$ is hydrogen atom or trifluoromethyl group, or a group represented by the formula:

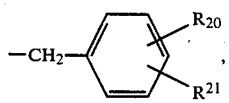

wherein $R^{20}$ and $R^{21}$ are hydrogen atoms or when taken together represent the group having the formula: —OCH2O—, or salts thereof, a process for preparing the same and antibacterial agents containing the same as an effective component.

The rifamycin derivative of the present invention is a novel compound which has not yet been reported in the literature.

SUMMARY OF THE INVENTION

According to the present invention, there are provided a rifamycin derivative having the general formula (I):

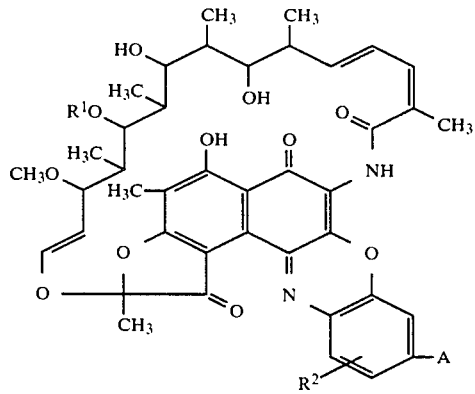

wherein $R^1$ is hydrogen atom or acetyl group; $R^2$ is hydrogen atom or hydroxyl group; A is a group represented by the formula:

wherein $R^3$ is an alkyl group with 1 to 5 carbon atoms or an alkoxyalykyl group wih 2 to 6 carbon atoms and $R^4$ is an alkyl group with 1 to 5 carbon atoms, a group represented by the formula: $—CH_2)_aX^1$, wherein a is 1 to 4 and $X^1$ is ethynyl group, cyano group, a group having the formula:

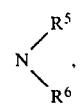

wherein $R^5$ and $R^6$ are the same or different from each other and are hydrogen atom or an alkyl group with 1 to 3 carbon atoms, a group represented by the formula: $OR^7$, wherein $R^7$ is hydrogen atom or an alkyl group having 1 to 4 carbon atoms, a group represented by the formula:

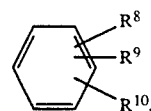

wherein $R^8$, $R^9$ and $R^{10}$ are the same or different from each other and are hydrogen atom or an alkoxy group with 1 to 3 carbon atoms, or a group represented by the formula:

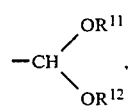

wherein $R^{11}$ and $R^{12}$ are the same or different from each other and are an alkyl group with 1 to 3 carbon atoms; a cycloalkyl group with 3 to 8 carbon atoms, a group represented by the formula:

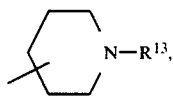

wherein $R^{13}$ is hydrogen atom or an alkyl group with 1 to 3 carbon atoms, or a group represented by the formula: $-CH_2(CHOH)_4CH_2OH$; a group represented by the formula:

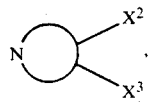

wherein

is a 3 to 10 memebered cyclic amino group with 2 to 9 carbon atoms, $X^2$ is hydrogen atom or an alkyl group having 1 to 4 carbon atoms and $X^3$ is hydrogen atom, an alkyl group with 1 to 3 carbon atoms, hydroxyl group, a group represented by the formula:

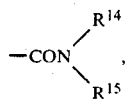

wherein $R^{14}$ and $R^{15}$ are the same or different from each other and are hydrogen atom or an alkyl group with 1 to 4 carbon atoms, a hydroxyalkyl group with 1 to 3 carbon atoms or cyclic or noncyclic amino group having 2 to 6 carbon atoms, or $X^2$ and $X^3$ when taken together represent =O group or the group represented by the formula: $-O(CH_2)_bO-$, wherein b is 2 to 4, a group represented by the formula:

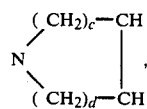

wherein c and d are the same or different from each other and are 1 to 4, a group represented by the formula:

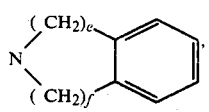

wherein e and f are the same or different from each other and are 1 to 4, or a group represented by the formula:

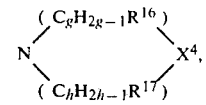

wherein g and h are the same or different from each other and are 1 to 4, $R^{16}$ and $R^{17}$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group having 1 to 3 carbon atoms, a phenyl group represented by the formula:

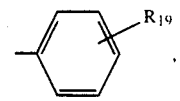

wherein $R^{19}$ is hydrogen atom or trifluromethyl group, or a group represented by the formula:

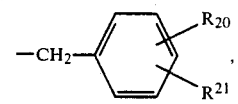

wherein $R^{20}$ and $R^{21}$ are hydrogen atoms or when taken together represent the group having the formula: $-OCH_2O-$, or salts thereof, a process for preparing the same and antibacterial agents containing the same as an effective component.

DETAILED DESCRIPTION OF THE INVENTION

As the result of the present inventors study, it was found that a rifamycin derivative having the general formula (I):

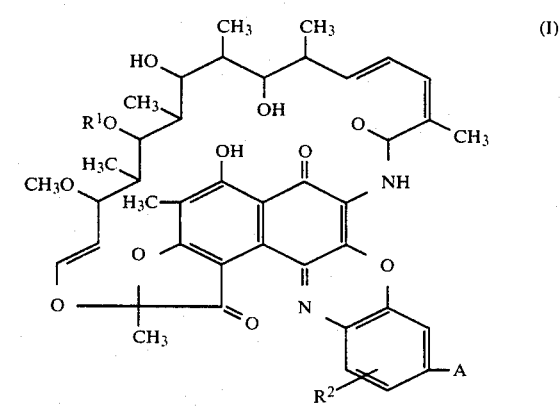

wherein $R^1$, $R^2$ and A are as defined above, could be prepared by reacting a rifamycin derivative having the general formula (II):

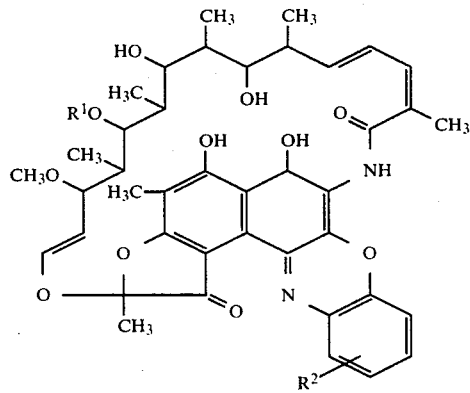

(II)

wherein $R^1$ and $R^2$ are as defined above, with an amine having the general formula: AH, wherein A is as defined above and the obtained rifamycin derivative having the general formula (I) possesses a high degree of activity against a large number of microorganisms.

The rifamycin derivative having the general formula (I) is soluble in various kinds of organic solvents, e.g. halogenated hydrocarbons such as chloroform, alcohols such as ethanol, esters such as ethyl acetate, aromatic hydrocarbons such as benzene and ethers such as tetrahydrofuran.

The rifamycin derivative of the present invention having the general formula (I) can form a salt with both base and acid. Any base or acid which can form a salt with the rifamycin derivative having the general formula (I) may be employed. Examples of the salt with base are metallic salt, especially alkali metal salt or alkaline earth metal salt, ammonium salt and amine salt, especially a salt with methylamine, ethylamine, diethylamine, triethylamine, pyrrolidine, morpholine or hexamethyleneimine.

Examples of the salt with acid are a salt with mineral acid such as sulfuric acid or hydrochloric acid and a salt with organic acid such as p-toluenesulfonic acid, trifluoroacetic acid or acetic acid.

The rifamycin derivative of the present invention having the general formula (I) can be prepared by reacting the rifamycin derivative having the general formula (II) dissolved in an organic solvent such as methanol, ethanol, tetrahydrofuran, N,N-dimethylformamide or dimethylsulfoxide with the amine having the general formula: AH, wherein A is as defined above, in the presence or absence of acid such as hydrochloric acid at a temperature of from $-20°$ C. to a boiling point of the solvent for 1 hour to 1 month and in the presence or absence of oxidizing agents.

Examples of the reaction solvent employed in the present invention are, for instance, methanol, ethanol, isopropyl alcohol, tetrahydrofuran, pyridine, acetone, ethyl acetate, chloroform, N,N-dimethylformamide, dimethylsulfoxide, and the like. Among them, pyridine, N,N-dimethylformamide or dimethylsulfoxide is preferably employed in the present invention with an excellent result.

The reaction is carried out at a temperature ranging from $-20°$ C. to a boiling point of the solvent, preferably from $-5°$ to $50°$ C.

Though the reaction may be carried out for around 1 hour to around 1 month, the optimum reaction time should be determined by following the proceeding of the reaction by thin layer chromatography and the like since it varies depending on a kind and an amount of the amine employed in the present invention, the presence or absence of oxidizing agent, a kind and an amount thereof, when present, the reaction temperature and the like.

When the reaction is carried out in the presence of the oxidizing agent, air, oxygen, manganese dioxide, lead dioxide, silver oxide, potassium ferricyanide, hydrogen peroxide and the like are employed as the oxidizing agent. Among them, manganese dioxide, silver oxide or potassium ferricyanide is preferably employed in the present invention with an excellent result.

The rifamycin derivative having the general formula (I), wherein $R^1$ is hydrogen atom and $R^2$ and A are as defined above, can also be prepared by hydrolyzing the rifamycin derivative having the general formula (I), wherein $R^1$ is acetyl group and $R^2$ and A are as defined above, with acid or base. Examples of acid employed for hydrolysis are, for instance, a mineral acid such as sulfuric acid or hydrochloric acid and an organic acid such as p-toluenesulfonic acid or trifluoroacetic acid. Examples of base employed for hydrolysis are, for instance, alkali metal hydroxide such as sodium hydroxide or potassium hydroxide, alkaline earth metal hydroxide such as calcium hydroxide or barium hydroxide, and an organic base such as 1,5-diazabicyclo[4.3.0]non-5-ene or 1,8-diazabicyclo[5.4.0]undec-7-ene.

Preferably the hydrolysis reaction is carried out at room temperature employing alkali metal hydroxide such as sodium hydroxide or potassium hydroxide and a solvent such as water-containing methanol or water-containing pyridine.

The rifamycin derivative of the present invention having the general formula (I), which is a dark purple solid, can be separated and purified from the reaction products in a relatively easy manner, i.e. an excess amount of the amine having the formula: AH and the reaction solvent are removed from the reaction system to give a crude product, which is then purified by crystallization, column-chromatography and the like.

The rifamycin derivative of the present invention having the general formula (I) can also be converted to the rifamycin derivative having the general formula (III):

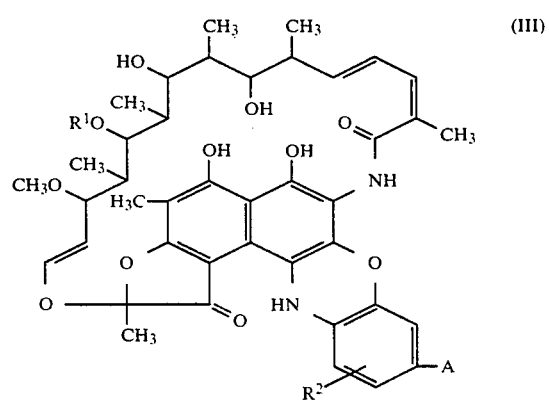

(III)

wherein $R^1$, $R^2$ and A are as defined above, by reducing the rifamycin derivative having the general formula (I) with reducing agent such as ascorbic acid, sodium hydrosulfite or the like.

Typical examples of the rifamycin derivative of the present invention having the general formula (I) are shown in Table 1.

TABLE 1

| Derivative No. | R¹ | R² | R³ | A R⁴ | Crystal form | Thin layer chromatography Rf | Solvent system* | Infrared absorption spectrum (cm⁻¹) | Chemical shift of nuclear magnetic resonance spectrum derived from the amine induced (δ,ppm)** |
|---|---|---|---|---|---|---|---|---|---|
| 1 | COCH₃ | H | CH₃ | CH₃ | flake | 0.26 | B | 1600 (C=O) | 3.16 (CH₃,6H,s) |
| 2 | COCH₃ | H | CH₃ | C₂H₅ | flake | 0.33 | B | 1600 (C=O) | 1.27 (CH₃,3H,t), 3.13 (CH₃,3H,s) and 3.56 (CH₂,2H,q) |
| 3 | COCH₃ | H | C₂H₅ | C₂H₅ | flake | 0.39 | B | 1600 (C=O) | 1.28 (CH₃,6H,s) and 3.54 (CH₂,4H,q) |
| 4 | COCH₃ | H | C₃H₇ | C₃H₇ | flake | 0.43 | B | 1601 (C=O) | 1.00 (CH₃,6H,t) and 3.37 —NCH₂—,4H,br) |
| 5 | COCH₃ | H | CH₃ | CH₂CCH | flake | 0.36 | B | 1604 (C=O) | 3.15 (CH₃,3H,s) |
| 6 | COCH₃ | H | CH₃ | CH₂CH₂CN | needle | 0.31 | C | 1601 (C=O) | 2.73 (CH₂,2H,br) and 3.27 (CH₁,3H,s) |
| 7 | COCH₃ | H | CH₃ | CH₂CH₂N(CH₃)₂ | amorphous | 0.34 | D | 1600 (C=O) | 2.33 (N(CH₃)₂,6H,s) and 3.15 (N—CH₃,3H,s) |
| 8 | COCH₃ | H | CH₃ | CH₂CH₂OH | amorphous | 0.43 | D | 1606 (C=O) | 3.20 (CH₃,3H,s) and 3.73 (CH₂CH₂,4H,d) |
| 9 | COCH₃ | H | CH₂CH₂OC₂H₅ | CH₂CH₂OC₂H₅ | needle | 0.32 | B | 1601 (C=O) | 1.20 (CH₃,6H,t), 3.47 (—OCH₂CH₃,4H,q) and 3.67 (NCH₂CH₂O,8H,br) |
| 10 | COCH₃ | H | CH₂CH₂CH₂OCH₃ | CH₂ benzene with OCH₃,OCH₃,OCH₃ | amorphous | 0.37 | B | 1598 (C=O) | 3.34 (CH₂OCH₃,3H,s), 3.80, OCH₃ (benzene with OCH₃,3H,s, OCH₃,3H,s, OCH₃); 3.83 (benzene with OCH₃,OCH₃,OCH₃,3H,s); 4.67 (CH₂,2H,s) |
| 11 | COCH₃ | H | CH₃ | CH₂CH(OCH₃)₂ | amorphous | 0.29 | B | 1600 (C=O) | 3.2 (CH₃,3H,s) and 3.43 (OCH₃,6H,s) |

TABLE 1-continued

| Derivative No. | $R^1$ | $R^2$ | $R^3$ | A $R^4$ | Crystal form | Thin layer chromatography Rf | Solvent system* | Infrared absorption spectrum (cm$^{-1}$) | Chemical shift of nuclear magnetic resonance spectrum derived from the amine induced (δ, ppm)** |
|---|---|---|---|---|---|---|---|---|---|
| 12 | COCH$_3$ | H | CH$_3$ | cyclohexyl | amorphous | 0.40 | B | 1602 (C=O) | 3.06 (CH$_3$, 3H, s) |
| 13 | COCH$_3$ | H | CH$_3$ | 1-methylpiperidin-4-yl | flake | 0.27 | D | 1602 (C=O) | 3.03 (N–CH$_3$, NCH$_3$, 3H, s) |
| 14 | COCH$_3$ | H | CH$_3$ | CH$_2$(CHOH)$_4$CH$_2$OH | amorphous | 0.13 | D | 1608 (C=O) | 3.27 (CH$_3$, 3H, s) |
| 15 | COCH$_3$ | H | | aziridin-1-yl | amorphous | 0.33 | B | 1606 (C=O) | 3.30 (CH$_2$CH$_2$, 4H, br) |
| 16 | COCH$_3$ | H | | 2-methylaziridin-1-yl | amorphous | 0.15 | A | 1602 (C=O) | 1.43 (CH$_3$, 3H, d) and 3.30 (CH$_2$, 2H, br) |
| 17 | COCH$_3$ | H | | azetidin-1-yl | flake | 0.30 | B | 1610 (C=O) | 4.20 (CH$_2$N–CH$_2$, 4H, t) |
| 18 | COCH$_3$ | H | | pyrrolidin-1-yl | flake | 0.29 | B | 1600 (C=O) | 3.55 (CH$_2$NCH$_2$, 4H, br) |
| 19 | COCH$_3$ | H | | piperidin-1-yl | flake | 0.34 | B | 1600 (C=O) | 3.53 (CH$_2$NCH$_2$, 4H, br) |

TABLE 1-continued

| Derivative No. | R¹ | R² | R³ A R⁴ | Crystal form | Thin layer chromatography Rf | Solvent system* | Infrared absorption spectrum (cm⁻¹) | Chemical shift of nuclear magnetic resonance spectrum derived from the amine induced (δ,ppm)** |
|---|---|---|---|---|---|---|---|---|
| 20 | COCH₃ | H | 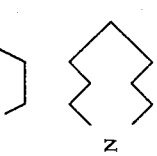 | amorphous | 0.45 | C | 1600 (C=O) | 3.53 (CH₂NCH₂,4H,br) |
| 21 | COCH₃ | H | 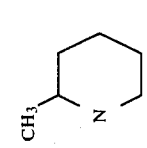 | amorphous | 0.39 | B | 1604 (C=O) | 3.67 (CH₂NCH₂,4H,br) |
| 22 | COCH₃ | H | 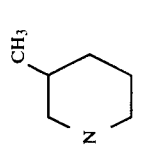 | flake | 0.16 | A | 1600 (C=O) | 1.27 (CH₃,3H,d) |
| 23 | COCH₃ | H | 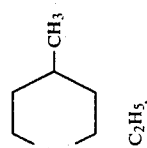 | flake | 0.35 | B | 1602 (C=O) | 1.00 (CH₃,3H,d) |
| 24 | COCH₃ | H | 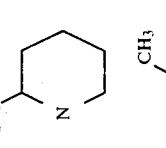 | flake | 0.35 | B | 1600 (C=O) | 1.03 (CH₃,3H,d) |
| 25 | COCH₃ | H | 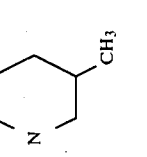 | flake | 0.22 | A | 1600 (C=O) | 0.95 (CH₃,3H,m) |
| 26 | COCH₃ | H |  | needle | 0.24 | A | 1600 (C=O) | 1.03 (CH₃,6H,d) |

TABLE 1-continued

| Derivative No. | R¹ | R² | R³ | A R⁴ | Crystal form | Thin layer chromatography Rf | Solvent system* | Infrared absorption spectrum (cm⁻¹) | Chemical shift of nuclear magnetic resonance spectrum derived from the amine induced (δ,ppm)** |
|---|---|---|---|---|---|---|---|---|---|
| 34 | COCH₃ | H | | piperidinyl-piperidine | flake | 0.33 | D | 1599 (C=O) | 1.53 (C$\underline{H_2}$CH₂C$\underline{H_2}$,6H,br) |
| 35 | COCH₃ | H | | 1,4-dioxa-8-azaspiro[4.5]decane | flake | 0.31 | B | 1599 (C=O) | 4.00 (OC$\underline{H_2}$C$\underline{H_2}$O,4H,s) |
| 36 | COCH₃ | H | | 4-oxopiperidine | flake | 0.21 | B | 1601 (C=O) | 2.67 (C$\underline{H_2}$CC$\underline{H_2}$,4H,t) and 3.95 (C$\underline{H_2}$NC$\underline{H_2}$,4H,br) |
| 37 | COCH₃ | H | | 1,2,3,6-tetrahydropyridine | flake | 0.43 | C | 1600 (C=O) | 3.70 and 4.00 (C$\underline{H_2}$NC$\underline{H_2}$,4H,br) |
| 38 | COCH₃ | H | | tetrahydroisoquinoline | flake | 0.43 | B | 1600 (C=O) | 3.75 (NC$\underline{H_2}$C$\underline{H_2}$,2H,br) and 7.16 (aromatic,4H,s) |
| 39 | COCH₃ | H | | N-methylpiperazine | flake | 0.32 | D | 1600 (C=O) | 2.63 (C$\underline{H_2}$N(CH₃)C$\underline{H_2}$,4H,br) and 3.63 (N(CH₂CH₂)₂NCH₃,4H,br) |
| 40 | COCH₃ | H | | 3,5-dimethylpiperazine | flake | 0.34 | D | 1600 (C=O) | 1.20 (C$\underline{H_3}$,6H,d) and 3.80 (C$\underline{H_2}$NC$\underline{H_2}$,4H,d) |

TABLE 1-continued

| Derivative No. | R¹ | R² | R³ | A / R⁴ | Crystal form | Thin layer chromatography Rf | Solvent system* | Infrared absorption spectrum (cm⁻¹) | Chemical shift of nuclear magnetic resonance spectrum derived from the amine induced (δ,ppm)** |
|---|---|---|---|---|---|---|---|---|---|
| 41 | COCH₃ | H | | 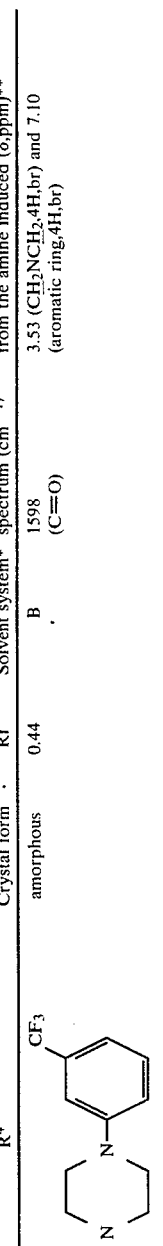 | amorphous | 0.44 | B | 1598 (C=O) | 3.53 ($CH_2NCH_2$,4H,br) and 7.10 (aromatic ring,4H,br) |
| 42 | COCH₃ | H | |  | flake | 0.28 | B | 1602 (C=O) | 5.93 ($CH_2$ 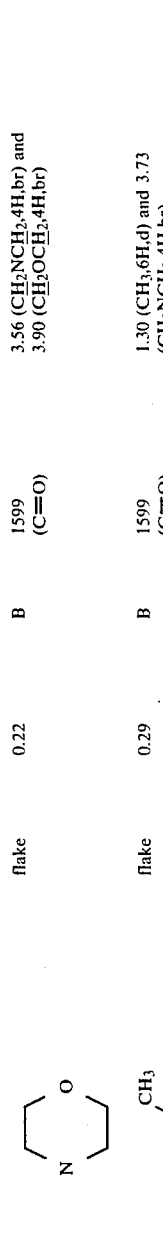 ,2H,s), 6.72 (aromatic ring,2H,s) and 6.83 (aromatic ring,1H,s) |
| 43 | COCH₃ | H | |  | flake | 0.22 | B | 1599 (C=O) | 3.56 ($CH_2NCH_2$,4H,br) and 3.90 ($CH_2OCH_2$,4H,br) |
| 44 | COCH₃ | H | |  | flake | 0.29 | B | 1599 (C=O) | 1.30 ($CH_3$,6H,d) and 3.73 ($CH_2NCH_2$,4H,br) |
| 45 | COCH₃ | H | | 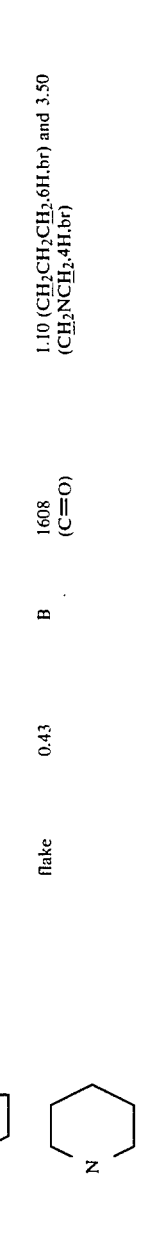 | flake | 0.34 | B | 1601 (C=O) | 2.73 ($CH_2SCH_2$,4H,br) and 3.90 ($CH_2NCH_2$,4H,br) |
| 46 | COCH₃ | OH | |  | flake | 0.28 | B | 1610 (C=O) | 3.20 ($CH_2NCH_2$,4H,b) |
| 47 | COCH₃ | OH | |  | flake | 0.43 | B | 1608 (C=O) | 1.10 ($CH_2CH_2CH_2$,6H,br) and 3.50 ($CH_2NCH_2$,4H,br) |

TABLE 1-continued

| Derivative No. | R¹ | R² | R³ | A R⁴ | Crystal form | Thin layer chromatography Rf | Solvent system* | Infrared absorption spectrum (cm⁻¹) | Chemical shift of nuclear magnetic resonance spectrum derived from the amine induced (δ,ppm)** |
|---|---|---|---|---|---|---|---|---|---|
| 48 | COCH₃ | OH | |  | flake | 0.26 | D | 1610 (C=O) | 3.63 (C$\underline{H}_2$NC$\underline{H}_2$,4H,br) |
| 49 | H | H | |  | flake | 0.58 | C | 1601 (C=O) | 3.56 (C$\underline{H}_2$NC$\underline{H}_2$,4H,br) |
| 50 | H | H | |  | flake | 0.66 | C | 1596 (C=O) | 3.63 (C$\underline{H}_2$NC$\underline{H}_2$,4H,br) |
| 51 | H | H | | 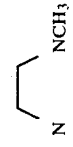 | flake | 0.23 | D | 1601 (C=O) | 3.63 (C$\underline{H}_2$NC$\underline{H}_2$,4H,br) |

*A: chloroform/acetone = 9/1
B: chloroform/acetone = 8/2
C: chloroform/acetone = 7/3
D: chloroform/methanol = 9/1
**s: singlet
d: doublet
t: triplet
q: quartet
m: multiplet
br: broad The rifamycin derivative of the present invention having the general formula (I) shows a strong antibacterial activity against the Gram-positive bacteria and the acid-fast bacteria. The antibacterial activity of the rifamycin derivative of the present invention having the general formula (I) is tested by the method according to the standard method of Japan Society of Chemotherapy [Chemotherapy (Tokyo), 29, P76, (1981)]. The results obtained from the typical compounds are shown in Table 2 as the minimum inhibitory concentration (MIC, μg/ml). As shown in Table 2, it is clear that the rifamycin derivative of the present invention shows a strong antibacterial activity against the Gram-positive bacteria and the acid-fast bacteria. In Table 2, Test compound No. corresponds to derivative No. in Table 1.

It was also found that the rifamycin derivative of the present invention having the general formula (I) had a low toxicity since toxicity was never exhibited by oral administration of 1000 mg/kg weight of the rifamycin derivative of the present invention having the general formula (I) to mice.

TABLE 3-continued

| Derivative No. | Dose (mg/kg) | Concentration in serum (μg/ml) | | |
|---|---|---|---|---|
| | | 1 hr. | 3 hrs. | 5 hrs. |
| compound) | | | | | n.d.: not detected

Antibacterial agents containing the rifamycin derivative of the present invention as an effective component can be in any dosage form of an oral, rectal, topical or parenteral administration. Examples of the dosage form are, for instance, tablets, capsules, granules, syrups, suppositories, ointments and the like. Carrier used in the dosage form of the antibacterial agents of the present invention is usually inactive pharmaceutical carrier of an organic or an inorganic solid or liquid suitable for an oral, rectal, topical or parenteral administration such as, for instance, crystalline cellulose, gelatin, lactose, starch, magnesium sterate, talc, plant or animal fat or oil, gum or polyalkylene glycol. A ratio of the antibacterial agent of the present invention to the carrier in the

TABLE 2

| Test organism | Test compound | | | | | | | | | | |
|---|---|---|---|---|---|---|---|---|---|---|---|
| | 2 | 3 | 4 | 9 | 11 | 12 | 17 | 18 | 19 | 20 | 23 |
| *Micrococcus luteus* IFO 12708 | 0.02≧ | 0.02≧ | 0.02≧ | 0.02≧ | 0.02≧ | 0.02≧ | 0.02≧ | 0.02≧ | 0.02≧ | 0.02≧ | 0.02≧ |
| *Bacillus subtilis* IFO 3134 | 0.04 | 0.02≧ | 0.08 | 0.02≧ | 0.02≧ | 0.02≧ | 0.02≧ | 0.02≧ | 0.02≧ | 0.04 | 0.02≧ |
| *Staphylococcus aureus* IFO 12732 | 0.02≧ | 0.02≧ | 0.02≧ | 0.02≧ | 0.02≧ | 0.02≧ | 0.02≧ | 0.02≧ | 0.02≧ | 0.08 | 0.02≧ |
| *Escherichia coli* IFO 12734 | 1.25 | 2.5 | >10 | 5 | >10 | >10 | 2.5 | 2.5 | 2.5 | 1.25 | >10 |
| *Klebsiella pneumoniae* IFO 3512 | 2.5 | 5 | >10 | 10 | 5 | >10 | 2.5 | 5 | 10 | >10 | >10 |
| *Mycobacterium smegmatis* ATCC 607 | 1.25 | 1.25 | 1.25 | 1.25 | 2.5 | 1.25 | 0.63 | 1.25 | 1.25 | 1.25 | 1.25 |

| Test organism | 24 | 27 | 31 | 37 | 39 | 45 | 46 | 49 | Rifampicin (control) |
|---|---|---|---|---|---|---|---|---|---|
| *Micrococcus luteus* IFO 12708 | 0.02≧ | 0.02≧ | 0.02≧ | 0.02≧ | 0.02≧ | 0.02≧ | 0.02≧ | 0.02≧ | 0.02≧ |
| *Bacillus subtilis* IFO 3134 | 0.02≧ | 0.02≧ | 0.02≧ | 0.02≧ | 0.04 | 0.04 | 0.02≧ | 0.02≧ | 0.04 |
| *Staphylococcus aureus* IFO 12732 | 0.02≧ | 0.02≧ | 0.02≧ | 0.08 | 0.04 | 0.02≧ | 0.02≧ | 0.02≧ | 0.02≧ |
| *Escherichia coli* IFO 12734 | >10 | >10 | 5 | 2.5 | 0.63 | 2.5 | >10 | 1.25 | 10 |
| *Klebsiella pneumoniae* IFO 3512 | >10 | >10 | >10 | >10 | 1.25 | 10 | >10 | 5 | 5 |
| *Mycobacterium smegmatis* ATCC 607 | 1.25 | 1.25 | 1.25 | 1.25 | 1.25 | 1.25 | 1.25 | 1.25 | 10 |

The rifamycin derivative having the general formula (II), which is a starting material for preparing the rifamycin derivative of the present invention having the general formula (I), can scarcely be absorped after oral administeration, while the rifamycin derivative of the present invention having the general formula (I) is absorbed to show a high blood level. Typical compounds were tested employing Wister Strain male rats weighing 27 to 300 g and the results obtained are shown in Table 3.

TABLE 3

| Derivative No. | Dose (mg/kg) | Concentration in serum (μg/ml) | | |
|---|---|---|---|---|
| | | 1 hr. | 3 hrs. | 5 hrs. |
| 2 | 20 | 3.0 | 5.4 | 3.0 |
| 3 | 20 | 1.8 | 3.3 | 1.3 |
| 4 | 20 | 2.0 | 8.5 | 2.1 |
| 9 | 20 | 2.1 | 5.4 | 1.8 |
| 11 | 20 | 2.9 | 3.4 | 1.0 |
| 17 | 20 | 4.1 | 3.7 | 2.5 |
| 18 | 20 | 2.3 | 4.9 | 3.4 |
| 19 | 20 | 4.9 | 12.4 | 16.6 |
| 20 | 20 | 3.2 | 5.7 | 4.9 |
| 23 | 20 | 2.1 | 6.1 | 5.2 |
| 25 | 20 | 2.4 | 6.6 | 3.5 |
| 27 | 20 | 1.8 | 6.4 | 1.7 |
| 49 | 20 | 2.7 | 3.5 | 2.8 |
| 50 | 20 | 0.7 | 2.4 | 2.8 |
| Benzoxazino-rifamycin (known | 100 | n.d. | n.d. | n.d. | dosage form can vary from 0.2 to 100% by weight. The antibacterial agent of the present invention can contain another pharmaceutical component such as another antibacterial agent compatible with the antibacterial agent of the present invention. In this case, however, the antibacterial agent of the present invention is not necessarily the chief ingredient of the dosage form.

The antibacterial agent of the present invention is administered with such a dose that the desired activity is achieved without any side-effect. Though the actual dose should be determined according to the judgment of the doctor, around 10 mg to around 10 g, preferably around 20 mg to around 5 g per day of the antibacterial agent of the present invention is usually administered for adults. The antibacterial agent of the present invention can be administered in a pharmaceutical dosage unit containing 1 mg to 5 g, preferably 3 mg to 1 g of an effective component.

The present invention is more particularly described and explained by the following Examples. However, it should be understood that the present invention is not limited to such Examples and various changes and modifications can be made without departing from the scope and spirit of the present invention.

In the following Examples, infrared absorption spectrum was measured according to the potassium bromide tablet method. Thin layer chromatography was carried out using Silica gel 60 $F_{254}$ (E. Merck Co.) and the thin layer chromatography plate (20 cm×20 cm). Nuclear magnetic resonance spectrum was measured using tetramethylsilane as an internal standard and deuterated chloroform solution. Measurement of the visible absorption spectrum was conducted in a solvent of methanol.

EXAMPLE 1

[Synthesis of derivative No. 1]

A solution of 0.2 g of benzoxazinorifamycin, which was prepared according to the method described in *Helv. Chim. Acta*, 56, p 2369 (1973), in 7.0 ml of methanol was mixed with a solution of 0.2 g of dimethylamine hydrochloride and 0.28 ml of triethylamine. The mixture was stirred for 18 hours at room temperature. Ethyl acetate was added to the reaction mixture and the resultant was washed twice with a saturated NaCl solution, followed by distillation of a solvent under reduced pressure. The residue was subjected to silca-gel column-chromatography [adsorbent: Wakogel ® C-200, eluent: chloroform-acetone (90 : 10)] to give a fraction containing the desired derivative. A solvent of the fraction was distilled away under reduced pressure and the residue was subjected to silica-gel column-chromatography as above, followed by work-up of the resultant to give 53 mg of a pure derivative No. 1.

Infrared absorption spectrum ($\nu$ cm$^{-1}$): 3450, 2960, 2930, 1720, 1660, 1600, 1560, 1490, 1460, 1410, 1360, 1310, 1260, 1200, 1170, 1120, 1060, 1040, 980, 950, 910, 820, 770 and 700.

Rf=0.26, blue spot [chloroform-acetaone (80 : 20)].

Nuclear magnetic resonance spectrum $\delta$ (ppm) (CDCl$_3$): 0.55, 0.80, 0.95 (CHCH$_3$), 2.05, 2.10, 2.15, 2.20, 3.05, 3.16 (CH$_3$), around 4.80 to 5.20 (protons at 25-postion and 28-position), around 5.90 to 6.20, 6.55, 6.75, 6.85, 7.80 (protons at 17-position, 19-position and 29-position and protons of benzoxazine ring), 7.75 (amide proton) and 15.1 (phenolic proton).

Visible absorption spectrum [$\delta$max. nm (E$_1$ $_{cm}$$^{1\%}$)]: 361 (154), 481 (51) and 633 (436).

Elementary analysis for C$_{45}$H$_{53}$N$_3$O$_{12}$. Calcd.(%): C 65.28, H 6.45, N 5.08. Found (%): C 65.35, H 6.51, N 5.01.

EXAMPLE 2

[Synthesis of derivative No. 2]

A solution of 1.0 g of benzoxazinorifamycin in 5 ml of dimethylsulfoxide (hereinafter referred to as "DMSO") was mixed with 0.22 ml of ethylmethylamine and 1.0 g of manganese dioxide. The mixture was stirred at room temperature for 5 hours. After completion of the reaction, the reaction mixture was diluted by addition of 50 ml of ethyl acetate and then maganese dioxide was filtered. A filtrate was washed successively with water (twice), diluted hydrochloric acid (twice) and water (twice) and a solvent was distilled away under reduced pressure. The residue was subjected to silica-gel column-chromatography (filler: Walpgel ® C-200, developer: ethyl acetate) to give a fraction containing the desired derivative. A solvent of the fraction was distilled away under reduced pressure and the obtained residue was dissolved in ethyl acetate, to which n-hexane was added to crystallize 0.73 g of the desired derivative No 2.

Infrared absorption spectrum ($\nu$ cm$^{-1}$): 3460, 2960, 2930, 1715, 1655, 1600, 1560, 1490, 1460, 1415, 1390, 1375, 1350, 1305, 1255, 1170, 1125, 1080, 1060, 1035, 970, 940, 910, 895, 815, 762, 695 and 440.

Nuclear magnetic resonance spectrum $\delta$ (ppm) (CDCl$_3$): 0.55, 0.78, 0.93 (CHCH$_3$), 1.27 (—NCH$_2$CH$_3$), 1.80, 2.01, 2.11, 2.14, 3.04 (CH$_3$), 3.13 (N—CH$_3$), 3.56 (—NCH$_2$CH$_3$), around 4.85 to 5.20 (protons at 25-position and 28-position), around 5.85 to 6.15, 6.53, 6.76, 6.86, 7.78 (protons at 17-position, 19-position and 29-position and protons of benzoxazine ring), 7.68 (amide proton) and 15.07 (phenolic proton).

Visible absorption spectrum [$\delta$max. nm (E$_1$ $_{cm}$$^{1\%}$)]: 363 (176), 480 (53) and 637 (504)

Elementary analysis for C$_{46}$H$_{55}$N$_3$O$_{12}$: Calcd.(%): C 65.62, H 6.59, N 4.99. Found (%): C 65.42, H 6.71, N 5.15.

EXAMPLE 3

[Synthesis of derivative No. 3]

A solution of 2.0 g of benzoxazinorifamycin in 10 ml of DMSO was mixed with 0.53 ml of diethylamine and 2.0 g of manganese dioxide. The mixture was stirred at room temperature for two days. After completion of the reaction, the procedure of Example 2 was repeated to give 0.79 g of the desired derivative No. 3.

Infrared absorption spectrum ($\nu$ cm$^{-1}$): 3450, 2970, 2940, 1715, 1663, 1650, 1600, 1560, 1520, 1490, 1470, 1403, 1380, 1355, 1308, 1260, 1185, 1175, 1122, 1078, 1040, 975, 945, 920, 900, 820, 765, 695 and 445.

Nuclear magnetic resonance spectrum $\delta$ (ppm) (CDCl$_3$): 0.55, 0.76, 0.91 (CHCH$_3$), 1.28 (N—CH$_2$—CH$_3$), 1.79, 2.00, 2.10, 2.14, 3.03 (CH$_3$), 3.54 (N—CH$_2$—CH$_3$), around 4.80 to 5.15 (protons at 25-position and 28-position), around 5.85 to 6.15, 6.48, 6.75, 6.85, 7.71, 7.81 (protons at 17-position, 19-position and 29-position and protons of benzoxazine ring), 7.71 (amide proton) and 15.13 (phenolic proton).

Visible absorption spectrum [$\lambda$ max. nm (E$_1$ $_{cm}$$^{1\%}$)]: 363 (183), 480 (49) and 642 (546).

Elementary analysis for C$_{47}$H$_{57}$N$_3$O$_{12}$: Calcd.(%): C 65.95, H 6.71, N 4.91. Found (%): C 65.74, H 6.87, N 4.76.

EXAMPLE 4

[Synthesis of derivative No. 4]

A solution of 2.0 g of benzoxazinorifamycin in 10 ml of DMSO was mixed with a 0.70 ml of dipropylamine and 2.0 g of manganese dioxide. The mixture was stirred at room temperature for two days. After completion of the reaction, the procedure of Example 2 was repeated to give 0.72 g of the desired derivative No. 4.

Infrared absorption spectrum ($\nu$ cm$^{-1}$): 3460, 2960, 2930, 2870, 1718, 1645, 1601, 1562, 1520, 1488, 1465, 1405, 1365, 1310, 1280, 1240, 1170, 1125, 1100, 1060, 1035, 975, 945, 925, 910, 845, 820, 770 and 450.

Nuclear magnetic resonance spectrum $\delta$ (ppm) (CDCL$_3$): 0.56, 0.75, 0.92 (CHCH$_3$), 1.00 (NCH$_2$CH$_2$CH$_3$), around 1.45 to 2.25 (N—CH$_2$CH$_2$CH$_3$), 1.79, 2.00, 2.09, 2.17, 3.03 (CH$_3$), 3.37 (N—CH$_2$CH$_2$CH$_3$), around 4.75 to 5.15, (protons at 25-position and 28-position), around 5.75 to 6.15, 6.44, 6.72, 6.83, 7.35, 7.44 (protons at 17-position, 19-position and 29-position and protons of benzoxazine ring), 7.30 (amide proton) and 15.06 (phenolic proton).

Visible absorption spectrum [$\lambda$ max. nm (E$_1$ $_{cm}$$^{1\%}$)]: 364 (170), 482 (49) and 644 (519).

Elementary analysis for C$_{49}$H$_{61}$N$_3$O$_{12}$: Calcd.(%): C 66.57, H 6.96, N 4.75. Found (%): C 66.73, H 6.79, N 4.93.

EXAMPLE 5

[Synthesis of derivative No. 5]

A solution of 1.0 g of benzoxazinorifamycin in 5 ml of DMSO was mixed with 0.22 ml of N-methylpropagylamine and 1.0 g of manganese dioxide. The mixture was stirred at room temperature for 6 hours. After completion of the reaction, the procedure of Example 2 was repeated to give 0.09 g of the desired derivative No. 5.

EXAMPLE 6

[Synthesis of derivative No. 6]

A solution of 1.0 g of benzoxazinorifamycin in 5 ml of DMSO was mixed with 0.24 ml of 3-methylaminopropionitrile and 1.0 g of manganese dioxide. The mixture was stirred at room temperature for 3 days. After completion of the reaction, the procedure of Example 2 was repeated to give 0.61 g of the desired derivative No. 6.

EXAMPLE 7

[Synthesis of derivative No. 7]

A solution of 1.0 g of benzoxazinorfamycin in 10 ml of methanol was mixed with 1.65 ml of N,N,N'-trimethylethylenediamine and 2.2 ml of a solution of 1.2 N hydrochloric acid in methanol. The mixture was stirred at room temperature for 17 hours. To the reaction mixture was added 0.5 g of manganese dioxide and the mixture was stirred at room temperature for 5 minutes. The resultant was filtered and chloroform was added to the filtrate, which was then wahsed twice with a saturated NaCl solution. A solvent was distilled away under reduced pressure and the residue was purified by repeating the procedure of silica-gel column-chromatography [eluent: chloroform-methanol (90 : 10)]to give 0.32 g of a pure derivative No. 7.

Infrared absorption spectrum ($\nu$ cm$^{-1}$): 3450, 2980, 2950, 1720, 1660, 1600, 1560, 1500, 1460, 1420, 1390, 1370, 1310, 1250, 1200, 1170, 1130, 1110, 1060, 1040, 980, 950, 920, 820, 780 and 700.

Rf=0.34, blue spot [chloroform-methanol (90 : 10)].

Nuclear magnetic resonance spectfum $\delta$ (ppm) (CDCl$_3$): 0.50, 0.75, 0.90 (CHCH$_3$), 1.83, 1.86, 2.01, 2.15, 2.20, 2.33, 2.60, 3.02 (C$\underline{H}$ or protons of ethylenediamino group), around 4.85 to 5.20 (protons at 25-position and 28-position), around 5.90 to 6.90 (protons at 17-position, 19-position and 29-position and protons of benzoxazine ring), 7.75 (proton of benzoxazine ring), 8.06 (amide proton) and 15.2 (phenolic proton).

Visible absorption spectrum [$\lambda$ max. nm (E$_{1\,cm}$$^{1\%}$)]: 361 (150), 481 (56) and 630 (437).

Elementary analysis for C$_{48}$H$_{60}$N$_4$O$_{12}$: Calcd.(%): C 65.14, H 6.83, N 6.33. Found (%): C 65.07, H 6.71, N 6.42.

EXAMPLE 8

[Synthesis of derivative No. 8]

A solution of 1.0 g of benzoxazinorifamycin in 5 ml of DMSO was mixed with 0.21 ml of 2-(methylamino)ethanol and the mixture was stirred at room temperature for 8 hours. After completion of the reaction, the procedure of Example 2 was repeated to give 0.62 g of the desired derivative compound No. 8.

EXAMPLE 9

[Synthesis of derivative No. 9]

A solution of 1.0 g of benzoxazinorifamiycin in 5 ml of DMSO was mixed with 0.41 g of bis(ethoxyethyl)amine and the mixture was stirred at room temperature for two days. After completion of the reaction, the procedure of Example 2 was repeated to give 0.13 g of the desired derivative No. 9.

Infrared absorption spectrum ($\nu$ cm$^{-1}$): 3470, 2980, 2940, 2880, 1718, 1662, 1601, 1560, 1520, 1485, 1460, 1400, 1380, 1355, 1320, 1260, 1230, 1170, 1120, 1060, 1040, 980, 950, 915, 900, 810, 765, 695 and 445.

Nuclear magnetic resonance spectrum $\delta$ (ppm) (CDCl$_3$): 0.57, 0.75, 0.92 (CHCH$_3$), 1.20 —OCH$_2$CH$_3$, 1.78, 2.00, 2.10, 2.16, 3.05 (C$\underline{H}_3$), around 3.30 to 3.85 (—NC$\underline{H}_2$C$\underline{H}_2$OC$\underline{H}_2$CH$_3$), around 4.80 to 5.15 (protons at 25-position and $\overline{28}$-position), around 5.85 to 6.15, 6.57, 6.85, 6.96, 7.71, 7.81 (protons at 17-position, 19-position and 29-position and protons of benzoxazine ring), 7.55 (amide proton) and 15.00 (phenolic proton).

Visible absorption spectrum [$\lambda$ max. nm (E$_{1\,cm}$$^{1\%}$)]: 362 (156), 482 (54) and 635 (460).

Elementary analysis for C$_{51}$H$_{65}$N$_3$O$_{14}$. Calcd.(%): C 64.88, H 6.94, N 4.45 Found (%): C 64.70, H 6.84, N 4.68

EXAMPLE 10

[Synthesis of derivative No. 10]

A solution of 1.0 g of benzoxazinorifamiycin in 5 ml of DMSO was mixed with 0.64 ml of N-(3-methoxypropyl)-3,4,5-trimethoxybenzylamine and 1.0 g of manganese dioxide and the mixture was stirred at room temperature for two days. After completion of the reaction, the procedure of Example 2 was repeated to give 0.11 g of the desired derivative No. 10.

EXAMPLE 11

[Synthesis of derivative No. 11]

A solution of 1.0 g of benzoxazinorifamycin in 5 ml of DMSO was mixed with 0.33 ml of methylaminoacetaldehyde dimethyl acetal and 1.0 g of manganese dioxide and the mixture was stirred at room temperature for 24 hours. After completion of the reaction, the procedure of Example 2 was repeated to give 0.55 g of the desired derivative No. 11.

Infrared absorption spectrum $\nu$ −1: 3450, 2970, 2930, 2830, 1715, 1645, 1600, 1560, 1520, 1490, 1465, 1410, 1380, 1370, 1305, 1255, 1200, 1170, 1130, 1110, 1060, 1035, 975, 910, 855, 820, 765, 710 and 445.

Nuclear magnetic resonance spectrum $\delta$ (ppm) (CDCl$_3$): 0.53, 0.77, 0.93 (CHCH$_3$), 1.82, 2.01, 2.13, 2.14, 3.06 (CH$_3$), 3.20 (N-CH$_3$), $\overline{3.43}$ (OCH$_3$), 3.60 (—CH—(OCH$_3$)$_2$), 4.56 (—$\overline{N}$CH$_2$—), around 4.85 to 5.20 (protons at 25-position and 28-position), around 5.95 to 6.10, 6.60, 6.85, 6.96, 7.75, 7.85 (protons at 17-position, 19-position and 27-position and protons of benzoxazine ring), 7.58 (amide proton) and 14.9 (phenolic proton). 1 %

Visible absorption spectrum [$\lambda$ max. nm (E$_{1cm}$$^{1\%}$9 361 (154), 480 (58) and 630 (431).

Elementary analysis for C$_{48}$H$_{59}$N$_3$O$_{14}$. Calcd.(%): C 63.92, H 6.59, N 4.66. Found (%): C 64.10, H 6.73, N 4.54.

EXAMPLE 12

[Synthesis of derivative No. 12]

A solution of 1.0 g of benzoxazinorifamycin in 5 ml of DMSO was mixed with 0.33 ml of N-methylcyclohexylamine and 1.0 g of manganese dioxide and the mixture was stirred at room temperature for two days. After completion of the reaction, the procedure of Example 2 was repeated to give 0.27 g of the desired derivative No. 12.

EXAMPLE 13

[Synthesis of derivative No. 13]

A solution of 1.0 g benzoxazinorifamycin in 5 ml of DMSO was mixed with 0.37 ml of 1-methyl-4-(methylamino)piperidine and 1.0 g of manganese dioxide and the mixture was stirred at room temperature for two days. After completion of the reaction, the procedure of Example 2 was repeated to give 0.17 g of the desired derivative No. 13.

Example 14

[Synthesis of derivative No. 14]

A solution of 1.0 g of benzoxazinorifamycin in 5 ml of DMSO was mixed with 0.5 g of N-methyl-D-glucamine and 1.0 g of manganese dioxide and the mixture was stirred at room temperature for 4 hours. After completion of the reaction, the proedure of Example 2 was repeated to give 0.63 g of the desired derivative No. 14.

EXAMPLE 15

[Synthesis of derivative No. 15]

A solution of 1.0 g of benzoxazinorifamycin in 5 ml of DMSO was mixed with 0.13 ml of ethylenimine and 1.0 g of manganese dioxide and the mixture was stirred at room temperature for one day. After completion of the reaction, the procedure of Example 2 was repeated to give 0.28 g of the desired derivative No. 15.

EXAMPLE 16

[Synthesis of derivative No. 16]

A solution of 1.0 g of benzoxazinorifamycin in 5 ml of DMSO was mixed with 0.18 ml of propyleneimine and 1.0 g of manganese dioxide and the mixture was stirred over night at room temperature. Afer completion of the reaction, the procedure of Example 2 was repeated to give 0.1 g of the desired derivative No. 16.

EXAMPLE 17

[Synthesis of derivative No. 17]

A solution of 1.0 g of bezoxazinorifamycin in 5 ml of DMSO was mixed with 0.17 ml of trimethyleneimine and 1.0 g of manganese dioxide and the mixture was stirred at room temperature for 6 hours. After completion of the reaction, the procedure of Example 2 was repeated to give 0.35 g of the desired derivative No. 17.

Infrared absorption spectrum ($\nu$ cm$^{-1}$): 3450, 2970, 2940, 2870, 1720, 1650, 1610, 1565, 1498, 1470, 1400, 1380, 1312, 1260, 1175, 1135, 1115, 1065, 1040, 975, 950, 920, 825, 818, 765, 670 and 435.

Nuclear magnetic resonance spectrum $\delta$ (ppm) (CDCl$_3$): 0.52, 0.77, 0.94 (CHC$\underline{H}_3$), 1.25 (protons of azetidine ring), 1.80, 2.02, 2.08, 2.84, 3.05 (C$\underline{H}_3$), 4.20 (—C$\underline{H}_2$NC$\underline{H}_2$—), around 4.75 to 5.15 (protons at 25-position and 28-position), round 5.85 to 6.15, 6.20, 6.38, 6.48, 7.68, 7.77 (protons at 17-position, 19-position and 29-position and protons of benzoxazine ring), 7.72 (amide proton) and 15.07 (phenolic proton).

Visible absorption spectrum [$\lambda$ max. nm (E$_1$$^{1\%}$)]362 (178), 476 (58) and 640 (522)

Elementary analysis for C$_{46}$H$_{53}$N$_3$O$_{12}$. Calcd.(%): C 65.78, H 6.36, N 5.00. Found (%): C 65.89, H 6.50, N 4.86.

EXAMPLE 18

[Synthesis of derivative No. 18]

A solution of 0.8 g of benzoxazinorifamycin in 10 ml of DMSO was mixed with 0.83 ml of pyrrolidine and 1.7 ml of a solution of 1.2 N hydrochloric acid in methanol and the mixture was stirred at room temperature for 17 hours. After completion of the reaction, the procedure of Example 1 was repeated to give 0.07 g of the desired derivative No. 18.

Infrared absorption spectrum ($\nu$ cm$^{-1}$) 3450, 2970, 2920, 2850, 1720, 1660, 1600, 1550, ,1480, 1460, 1390, 1370, 1340. 1320, 1260, 1220, 1160, 1130, 1060, 1040, 980, 940, 920, 910, 860, 820, 770 and 600 , Rf=0.38, blue spot [chloroform-acetone (70 : 30)].

Nuclear magnetic resonance spectrum $\delta$ (ppm) (CDCl$_3$). 0.52, 0.80, 0.90 (CHC$\underline{H}_3$), 1.80, 2.00, 2.10, 2.18, 3.02, 3.55 (C$\underline{H}_3$ and protons of pyrrolidine ring), around 4.80 to 5.10 (protons at 25-position and 28-position), 5.95, 6.06, 6.50, 6.66, 6.75, 7.70 (protons at 17-position, 19-position and 29-position and protons of benzoxazine ring), 8.25 (amide proton) and 15.2 (phenolic proton).

Visible absorption spectrum [$\lambda$ max. n (E$_{1\,cm}$$^{1\%}$)]: 363 (138), 480 (43) and 642 (409).

Elementary analysis for C$_{47}$H$_{55}$N$_3$O$_{12}$: Calcd.(%): C 66.11, H 6.49, N 4.92. Found (%): C 66.03, H 6.56, N 4.84.

EXAMPLE 19

[Synthesis of deriative No. 19]

A solution of 5.5 g of benzoxazinorifamycin in 70 ml of methanol was mixed with 6.0 g of piperidine and 11.7 ml of a solution of 1.2 N hydrochloric acid in methanol and the mixture was stirred at room temperature for 7 hours. After completion of the reaction, 2.8 g of manganese dioxide was added to the reaction mixture and the mixture was stirred at room temperature for 5 minutes. The resultant was filtered and chloroform was added to the filtrate, which was then washed twice with a saturated NaCl solution. A solvent was distilled away under reduced pressure and the residue was treated as in Example 2 to give 0.5 g of the desired derivative No. 19.

Infrared absorption spectrum ($\nu$ cm$^{-1}$): 3450, 2950, 2930, 2870, 1720, 1650, 1600, 1560, 1485, 1460, 1395, 1370, 1305, 1240, 1210, 1170, 1115, 1060, 1020, 980, 950, 920, 900, 850, 820, 770, 690, 640 and 580.

Rf=0.45, blue spot [chloroform-aceton (70 : 30)].

Nuclear magnetic resonance spectrum $\delta$ (ppm) (CDCl$_3$): 0.53, 0.86, 0.93 (CHC$\underline{H}_3$), 1.73, 1.80, 2.00, 2.10, 2.48, 3.03, 3.53 (C$\underline{H}_3$ and protons of piperidine ring), around 4.85 to 5.06 (protons at 25-position and 28-position), 5.90, 6.03, 6.67, 6.69, 6.90, 7.00, 7.76 (protons at 17-position, 19-position and 29-position and protons of benzoxazine ring), 7.70 (amide proton) and 15.02 (phenolic proton).

Visible absorption spectrum [$\lambda$ max, nm (E$_{1\,cm}$$^{1\%}$)]: 363 (160), 481 (55) and 643 (488).

Elementary analysis for $C_{48}H_{57}N_3O_{12}$. Calcd.(%): C 66.42, H 6.62, N 4.84. Found (%): C 66.30, H 6.73, N 4.95.

EXAMPLE 20

[Synthesis of derivative No. 20]

A solution of 5.5 g of benzoxazinorifamycin in 70 ml of methanol was mixed with 7.0 g of hexamethyleneimine and 11.7 ml of a solution of 1.2 N hydrochloric acid in methanol and the mixture was stirred at room temperature for 6 hours. After completion of the reaction, the procedure of Example 19 was repeated to give 0.4 g of the desired derivative No. 20.

Infrared absorption spectrum ($\nu$ cm$^{-1}$): 3460, 2960, 2930, 1720, 1660, 1650, 1600, 1560, 1520, 1490, 1460, 1400, 1360, 1305, 1250, 1205, 1160, 1125, 1100, 1060, 1040, 1000, 975, 945, 900, 860, 820, 770, 690, 640 and 580.

Rf=0.45, blue spot [chloroform-acetone (70 : 30)].

Nuclear magnetic resonance spectrum $\delta$ (ppm) (CDCl$_3$): 0.53, 0.75, 0.92 (CH$CH_3$), 1.65, 1.83, 2.02, 2.13, 3.06, 3.53 (CH$_3$ and protons of hexamethyleneimine ring), around 4.85 to 5.10 (protons at 25-position and 28-position), 5.90, 6.05, 6.56, 6.59, 6.85, 6.92, 7.73, 7.85 (protons at 17-position, 19-position and 29-position and protons of benzoxazine ring), 7.67 (amide proton) and 15.13 (phenolic proton).

Visible absorption spectrum [$\lambda$ max. nm (E $_{1\ cm}^{1\%}$)]363 (178), 484 (55) and 644 (539).

Elementary analysis for $C_{49}H_{59}N_3O_{12}$: Calcd.(%): C 66.73, H 6.74, N 4.76. Found (%): C 66.86, H 6.67, N 4.84.

EXAMPLE 21

[Synthesis of derivative No. 21]

A solution of 5.5 g of benzoxazinorifamycin in 70 ml of methanol was mixed with 7.9 ml of heptamethyleneimino and 11.7 ml of a solution of 1.2 N hydrochloric acid in methanol and the mixture was stirred at room temperature for 6.5 hours. After completion of the reaction, the procedure of Example 19 was repeated to give 0.96 g of the desired derivative No. 21.

EXAMPLE 22

[Synthesis of derivative No. 22]

A solution of 1.0 g of benzoxazinorifamycin in 5 ml of DMSO was mixed with 0.3 ml of 2-methylpiperizine and 1.0 g of manganese dioxide and the mixture was stirred at room temperature for two days. After completion of the reaction, the procedure of Example 2 was repeated to give 0.34 g of the desired derivative No. 22.

EXAMPLE 23

[Synthesis of derivative No. 23]

A solution of 1.0 g of benzoxazinorifamycin in 5 ml of DMSO was mixed with 0.3 ml of 3-methylpiperidine and 1.0 g of manganese dioxide and the mixture was stirred at room temperature for 4 hours. After completion of the reaction, the procedure of Example 2 was repeated to give 0.46 g of the desired derivative No. 23.

Infrared absorption spectrum ($\nu$ cm$^{-1}$): 3450, 2970, 2940, 2880, 1720, 1650, 1602, 1560, 1490, 1460, 1400, 1380, 1310, 1245, 1220, 1175, 1125, 1090, 1065, 1040, 970, 905, 860, 820, 770, 645 and 590.

Nuclear magnetic resonance spectrum $\delta$ (ppm) (CDCl$_3$): 0.47, 0.77, 0.92 (CH$CH_3$), 1.00 (CH$_3$ of piperidine), around 1.45 to 2.25, around 2.55 to 3.25, around 3.75 to 4.10 (protons of piperidine ring), 1.80, 2.00, 2.10, 2.14, 3.03 (CH$_3$), around 4.85 to 5.15 (protons at 25-position and 28-position), around 5.85 to 6.15, 6.67, 6.90, 7.01, 7.72, 7.82 (protons at 17-position, 19-position and 29-position and protons of benzoxazine ring), 7.82 (amide proton) and 15.01 (phenolic proton).

Visible absorption spectrum [$\lambda$ max. nm (E $_{1cm}^{1\%}$)]363 (163), 481 (52) and 646 (498).

Elementary analysis for $C_{49}H_{59}N_3O_{12}$: Calcd.(%): C 66.73, H 6.74, N 4.76. Found (%): C 66.61, H 6.96, N 4.87.

EXAMPLE 24

[Synthesis of derivative No. 24]

A solution of 1.0 g of benzoxazinorifamycin in 5 ml of DMSO was mixed with 0.3 ml of 4-methylpiperidine and 1.0 g of manganese dioxide and the mixture was stirred at room temperature for 4 hours. After completion of the reaction, the procedure of Example 2 was repeated to give 0.74 g of the desired derivative No. 24.

EXAMPLE 25

[Synthesis of derivative No. 25]

A solution of 1.0 g of benzoxazinorifamycin in 5 ml of DMSO was mixed with 0.34 ml of 2-ethylpiperidine and 1.0 g of manganese dioxide and the mixture was stirred at room temperature for 5 days. After completion of the reaction, the procedure of Example 2 was repeated to give 0.22 g of the desired derivative No. 25.

EXAMPLE 26

[Synthesis of derivative No. 26]

A solution of 1.0 g of benzoxazinorifamycin in 5 ml of DMSO was mixed with 0.34 ml of 3,5-dimethylpiperidine and 1.0 g of manganese dioxide and the mixture was stirred at room temperature for 4 hours. After completion of the reaction, the procedure of Example 2 was repeated to give 0.77 g of the desired derivative No. 26.

EXAMPLE 27

[Synthesis of derivative No. 27]

A solution of 1.0 g of benzoxazinorifamycin in 5 ml of DMSO was mixed with 0.32 ml of 3,3-dimethylpiperidine and 1.0 g of manganese dioxide and the mixture was stirred at room temperature for 2 hours. After completion of the reaction, the procedure of Example 2 was repeated to give 0.73 g of the desired derivative No. 27.

Infrared absorption spectrum ($\nu$ cm$^{-1}$): 3460, 2940, 2870, 1720, 1660, 1600, 1560, 1485, 1460, 1398, 1375, 1305, 1245, 1205, 1160, 1130, 1080, 1055, 1025, 980, 945, 898, 860, 815, 765, 710, 640 and 590.

Nuclear magnetic resonance spectrum $\delta$ (ppm) (CDCl$_3$): 0.52, 0.77, 0.93 (CH$CH_3$), 1.00 (CH—(CH$_3$)$_2$), around 1.40 to 1.80 (protons of piperidine ring), 1.79, 2.00, 2.10, 2.15, 4.03 (CH$_3$), around 4.15 to 4.60 (protons of piperidine ring), around 4.80 to 5.15 (protons at 25-position and 28-position), around 5.85 to 6.15, 1.63, 6.86, 6.97, 7.78 (protons at 17-position, 19-position and 29-position and protons of benzoxazine ring), 7.68 (amide proton) and 15.08 (phenolic proton).

Visible absorption spectrum [$\lambda$ max. nm (E$_1$ $_{cm}^{1\%}$)]365 (164), 482 (50) and 648 (515).

Elementary analysis for $C_{50}H_{61}N_3O_{12}$: Calcd.(%): C 67.02, H 6.86, N 4.69. Found (%): C 67.12, H 6.74, N 4.55.

EXAMPLE 28

[Synthesis of derivative No. 28]

A solution of 1.0 g of benzoxazinorifamycin in 5 ml of DMSO was mixed with 0.26 g of 3-hydroxypiperidine and 1.0 g of manganese dioxide and the mixture was stirred at room temperature for 4 hours. After completion of the reaction, the procedure of Example 2 was repeated to give 0.65 g of the desired derivative No. 28.

EXAMPLE 29

[Synthesis of derivative No. 28]

A solution of 2.0 g of benzoxazinorifamycin in 25 ml of methanol was mixed with 2.58 g of 4-hydroxypiperidine and 4.25 ml of a solution of 1.2 N hydrochloric acid in methanol and the mixture was stirred at room temperature for 6.5 hours. After completion of the reaction, the procedure of Example 1 was repeated to give 0.92 g of the desired derivative No. 29.

EXAMPLE 30

[Synthesis of derivative No. 30]

A solution of 2.0 g of benzoxazinorifamycin in 25 ml of methanol was mixed with 3.27 g of nipecotamide and 4.25 ml of a solution of 1.2 N hydrochloric acid in methanol and the mixture was stirred at room temperature for 6.5 hours. After completion of the reaction, the procedure of Example 1 was repeated to give 0.86 g of the desired derivative No. 30.

EXAMPLE 31

[Synthesis of derivative No. 31]

A solution of 1.0 g of benzoxazinorifamycin in 5 ml of DMSO was mixed with 4.7 g of N,N-diethylnipecotamide and 1.0 g of manganese dioxide and the mixture was stirred at room temperature for 7 hours. After completion of the reaction, the procedure of Example 2 was repeated to give 0.33 g of the desired derivative No. 31.

EXAMPLE 32

[Synthesis of derivative No. 32]

A solution of 1.0 g of benzoxazinorifamycin in 5 ml of DMSO was mixed with 0.45 ml of 4-benzylpiperidine and 1.0 g of manganese dioxide and the mixture was stirred at room temperature for 2 hours. After completion of the reaction, the procedure of Example 2 was repeated to give 0.72 g of the desired derivative No. 32.

EXAMPLE 33

[Synthesis of derivative No. 33]

A solution of 1.0 g of benzoxazinorifamycin in 5 ml of DMSO was mixed with 0.29 g of 2-piperidinemethanol and 1.0 g of manganese dioxide and the mixture was stirred at room temperature for 11 days. After completion of the reaction, the procedure of Example 2 was repeated to give 0.25 g of the desired derivative No. 33.

EXAMPLE 34

[Synthesis of derivative No. 34]

A solution of 1.0 g of benzoxazinorifamycin in 5 ml of DMSO was mixed with 0.43 g of 4-piperidinopiperidine and 1.0 g of manganese dioxide and the mixture was stirred at room temperature for 4 hours. After completion of the reaction, the procedure of Example 2 was repeated to give 0.48 g of the desired derivative No. 34.

EXAMPLE 35

[Synthesis of derivative No. 35]

A solution of 1.0 g of benzoxazinorifamycin in 5 ml of DMSO was mixed with 0.33 ml of 1,4-dioxa-8-azaspiro[4.5] decane and 1.0 g of manganese dioxide and the mixture was stirred at room temperature for 2.5 hours. After completion of the reaction, the procedure of Example 2 was repeated to give 0.17 g of the desired derivative No. 35.

EXAMPLE 36

[Synthesis of derivative No. 36]

A solution of 5.11 g of benzoxazinorifamycin in 65 ml of methanol was mixed with 10 g of 4-piperidon monohydrate hydrochloride and 7.26 ml of triethylamine and the mixture was stirred at room temperature for 6.5 hours. After completion of the reaction, the procedure of Example 1 was repeated to give 0.33 g of the desired derivative No. 36.

EXAMPLE 37

[Synthesis of derivative No. 37]

A solution of 2.0 g of benzoxazinorifamycin in 25 ml of methanol was mixed with 2.33 ml of 1,2,3,6-tetrahydropyridine and 4.25 ml of a solution 1.2 N hydrochloric acid in methanol and the mixture was stirred at room temperature for 6.5 hours. After completion of the reaction, the procedure of Example 1 was repeated to give 0.38 g of the desired derivative No. 37.

EXAMPLE 38

[Synthesis of derivative No. 38]

A solution of 1.0 g of benzoxazinorifamycin in 5 ml of DMSO was mixed with 0.32 ml of 1,2,3,4-tetrahydroisoquinoline and 1.0 g of manganese dioxide and the mixture was stirred over night at room temperature. After completion of the reaction, the procedure of Example 2 was repeated to give 0.59 g of the desired derivative No. 38.

EXAMPLE 39

[Synthesis of derivative No. 39]

A solution of 2.0 g of benzoxazinorifamycin in 20 ml of methanol was mixed with 2.5 g of N-methylpiperazine and 4.2 ml of a solution of 1.2 N hydrochloric acid in methanol and the mixture was stirred at room temperature for 17 hours. After completion of the reaction, the procedure of Example 19 was repeated to give 0.98 g of the desired derivative No. 39.

Infrared absorption spectrum ($\nu$ cm$^{-1}$): 3450, 2970, 2940, 1720, 1660, 1600, 1560, 1480, 1460, 1420, 1400, 1370, 1300, 1250, 1220, 1170, 1130, 1080, 1040, 1020, 1000, 980, 950, 920, 900, 820, 770, 740, 700, 640, 610 and 510.

Rf=0.32, dark blue spot [chloroform-methanol (90 : 10)].

Nuclear magnetic resonance spectrum $\delta$ (ppm) (CDCl$_3$): 0.50, 0.72, 0.91 (CHCH$_3$), 1.80, 2.03, 2.11, 2.20, 2.23, 2.34, 2.63 and 3.03 (CH$_3$ or protons of piperazine ring), around 4.8 to 5.1 (protons at 25-position and 28-position), around 5.9 to 7.0 (protons at 17-position, 19-position and 29-position and protons of benzoxazine ring), 7.8 (proton of benzoxazine ring) and 14.95 (phenolic proton).

Visible absorption spectrum [λ max. nm (E $_{1\ cm}^{1\%}$)]357 (140), 482 (76) and 620 (378).

Elementary analysis for $C_{48}H_{58}N_4O_{12}$. Calcd.(%): C 65.29, H 6.62, N 6.35. Found (%): C 65.19, H 6.49, N 6.48.

EXAMPLE 40

[Synthesis of derivative No. 40]

A solution of 1.0 g of benzoxazinorifamycin in 5 ml of DMSO was mixed with 0.29 g of 2,6-dimethylpiperazine and 1.0 g of manganese dioxide and the mixture was stirred at room temperature for 4 hours. After completion of the reaction, the procedure of Example 2 was repeated to give 0.55 g of the desired derivative No. 40.

EXAMPLE 41

[Synthesis of derivative No. 41]

A solution of 1.0 g of benzoxazinorifamycin in 5 ml of DMSO was mixed with 0.48 ml of 1-[3-(trifluoromethyl)phenyl]piperazine and 1.0 g of manganese dioxide and the mixture was stirred at room temperature for 2 hours. After completion of the reaction, the procedure of Example 2 was repeated to give 0.49 g of the desired derivative No. 41.

EXAMPLE 42

[Synthesis of derivative No. 42]

A solution of 1.0 g of benzoxazinorifamycin in 5 ml of DMSO was mixed with 0.56 g of 1-piperonylpiperazine and 1.0 g of manganese dioxide and the mixture was stirred at room temperature for 4.5 hours. After completion of the reaction, the procedure of Example 2 was repeated to give 0.74 g of the desired derivative No. 42.

EXAMPLE 43

[Synthesis of derivative No. 43]

A solution of 1.57 g of benzoxazinorifamycin in 20 ml of methanol was mixed with 1.74 ml or morpholine and 3.3 ml of a solution of 1.2 N hydrochloic acid in methanol and the mixture was stirred at room temperature for 6.5 hours. After completion of the reaction, the procedure of Example 1 was repeated to give 0.39 g of the desired derivative No. 43.

EXAMPLE 44

[Synthesis of derivative No. 44]

A solution of 1.0 g of benzoxazinorifamycin in 5 ml of DMSO was mixed with 0.32 ml of 2,6-dimethylmorpholine and 1.0 g of manganese dioxide and the mixture was stirred at room temperature for 4.5 hours. After completion of the reaction, the procedure of Example 2 was repeated to give 0.20 g of the desired derivative No. 44.

EXAMPLE 45

[Synthesis of derivative No. 45]

A solution of 1.0 g of benzoxazinorifamycin in 5 ml of DMSO was mixed with 0.26 ml of thiomorpholine and 1.0 g of manganese dioxide and the mixture was stirred at room temperature for 5 hours. After completion of the reaction, the procedure of Example 2 was repeated to give 0.88 g of the desired derivative No. 45.

EXAMPLE 46

[Synthesis of benzoxazinorifamycin derivative represented by the formula (IV)]

A mixture of 2.42 g of 2-aminoresorcinol hydrochloride, 2.24 ml of triethylamine and 5 ml of chloroform was added 11 times at a thirty to fourty minutes' interval into a solution of 34.79 g of rifamycin S in 200 ml of chloroform while stirring the mixture. Both thirty minutes after the eighth addition of 2-aminoresorcinol and thirty minutes after the last addition of 2-aminoresorcinol, 30 g of manganese dioxide was added to the mixture. After completion of the reaction, the procedure of Example 2 was repeated to give 3.17 g of benzoxazinorifamycin derivative having the formula (IV).

Infrared absorption spectrum ($v$ cm$^{-1}$): 3450, 3260, 2970, 2930, 2880, 1700, 1660, 1615, 1598, 1565, 1525, 1495, 1455, 1420, 1370, 1340, 1310 1285, 1250, 1210, 1180, 1143, 1063, 1050, 1008, 975, 945, 908, 895, 810, 790, 770, 755, 660, 630 and 440.

Nuclear magnetic resonance spectrum δ (ppm) (CDCl$_3$): 0.40, 0.77, 0.93 (CHCH$_3$), 1.83, 2.02, 2.12, 2.27, 3.05 (CH$_3$), around 4.80 to 5.10 (protons at 25-position and 28-position), around 5.5 to 6.5 (protons at 17-position, 19-position and 29-position), 6.77, 6.90, 7.43 (protons of benzoxazine ring), 7.93 (amide proton), 9.92 and 14.33 (phenolic protons).

EXAMPLE 47

[Synthesis of derivative No. 46]

A solution of 0.8 g of the derivative represented by the formula (IV) prepared in Example 46 in 10 ml of DMSO was mixed with 0.15 g of pyrrolidine and 0.8 g of manganese dioxide and the mixture was stirred over night at room temperature. After completion of the reaction, the procedure of Example 2 was repeated to give 0.10 g of the desired derivative No. 46.

EXAMPLE 48

[Synthesis of derivative No. 47]

A solution of 0.8 g of the derivative represented by the formula (IV) prepared in Example 46 in 10 ml of DMSO was mixed with 0.17 g of piperidine and 0.8 g of manganese dioxide and the mixture was stirred over night at room temperature. After completion of the reaction, the procedure of Example 2 was repeated to give 0.37 g of the desired derivative No. 47.

EXAMPLE 49

[Synthesis of derivative No. 48]

A solution of 0.8 g of the derivative represented by the formula (IV) prepared in Example 46 in 10 ml of DMSO was mixed with 0.2 g of N-methylpiperazine and 0.8 g of manganese dioxide and the mixture was stirred at room temperature for two days. After completion of the reaction, the procedure of Example 2 was repeated to give 0.44 g of the desired derivative No. 48.

EXAMPLE 50

[Synthesis of derivative No. 49]

One gram of the derivative No. 18 prepared in Example 18 was added to a mixture of water and ethanol (1:1) containing 0.96 g of sodium hydroxide and the mixture was stirred at room temperature for 1.5 hours. After completion of the reaction, the reaction mixture was diluted with cold water, which was then neutralized with 1N hydrochloric acid solution and extracted with chloroform. The extract was evaporated to dryness under reduced pressure and the procedure of Example 2 was repeated to give 0.63 g of the desired derivative No. 49.

Infrared absorption spectrum ($\nu$ cm$^{-1}$): 3430, 2960, 2930, 2880, 1710, 1672, 1601, 1485, 1465, 1398, 1378, 1350, 1320, 1285, 1265, 1235, 1175, 1150, 1135, 1120, 1060, 1040, 980, 950, 910, 860, 825, 775, 660, 600 and 435.

Nuclear magnetic resonance spectrum $\delta$ (ppm) (CDCl$_3$): 0.82, 0.88, 0.93 (CHC$\underline{H}_3$), 1.83, 2.04, 2.18, 3.02 (CH$_3$), 2.85 to 3.85 (protons of pyrrolidine ring), around 4.90 to 5.30 (protons at 25-position and 28-position), 5.64, 5.77, around 6.00 to 6.50, 6.85 (protons at 17-position, 19-position and 29-position and protons of benzoxazine ring), 7.15 (amide proton) and 15.62 (phenolic proton).

Visible absorption spectrum [$\lambda$ max. nm (E$_{1\ cm}^{1\%}$)]: 363 (167), 478 (46) and 642 (516).

Elementary analysis for C$_{45}$H$_{53}$N$_3$O$_{11}$. Calcd.(%): C 66.57, H 6.58, N 5.17. Found (%): C 66.70, H 6.78, N 4.99.

EXAMPLE 51

[Synthesis of derivative No. 50]

The procedure of Example 50 was repeated except that 1.0 g of the derivative No. 19 was employed in place of the derivative No. 18 to give 0.59 g of the desired derivative No. 50.

EXAMPLE 52

[Synthesis of derivative No. 51]

The procedure of Example 50 was repeated except that 0.22 g of the derivative No. 39 was employed in place of the derivative No. 18 to give 0.13 g of the desired derivative No. 51.

What we claimed is:

1. A rifamycin compound having the formula (I):

wherein $R^1$ is hydrogen atom or acetyl group; $R^2$ is hydrogen atom or hydroxyl group; A is a group represented by the formula:

$$N\begin{matrix}R^3\\R^4\end{matrix}$$

wherein $R^3$ is an alkyl group with 1 to 5 carbon atoms or an alkoxyalkyl group with 2 to 6 carbon atoms and $R^4$ is an alkyl group with 1 to 5 carbon atoms, a group represented by the formula: —(CH$_2$)$_a$X$^l$, wherein a is 1 to 4 and X$^l$ is ethynyl group, cyano group, a group having the formula:

$$N\begin{matrix}R^5\\R^6\end{matrix}$$

wherein $R^5$ and $R^6$ are the same or different from each other and are hydrogen atom or an alkyl group with 1 to 3 carbon atoms, a group represented by the formula: OR$^7$, wherein R$^7$ is hydrogen atom or an alkyl group with 1 to 4 carbon atoms, a group represented by the formula:

wherein $R^8$, $R^9$ and $R^{10}$ are the same or different from each other and are hydrogen atom or an alkoxy group with 1 to 3 carbon atoms, or a group represented by the formula:

$$-CH\begin{matrix}OR^{11}\\OR^{12}\end{matrix}$$

wherein $R^{11}$ and $R^{12}$ are the same or different from each other and are an alkyl group with 1 to 3 carbon atoms; a cycloalkyl group with 3 to 8 carbon atoms, a group represented by the formula:

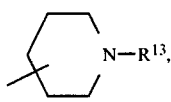

wherein $R^{13}$ is hydrogen atom or an alkyl group with 1 to 3 carbon atoms, or a group represented by the formula: —CH$_2$(CHOH)$_4$CH$_2$OH; a group represented by the formula:

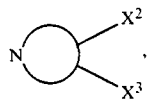

wherein

is a 3 to 10 membered cyclic amino group with 2 to 9 carbon atoms, $X^2$ is hydrogen atom or an alkyl group having 1 to 4 carbon atoms and $X^3$ is hydrogen atom, an alkyl group with 1 to 3 carbon atoms, hydroxyl group, a group represented by the formula:

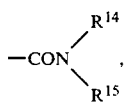

wherein $R^{14}$ and $R^{15}$ are the same or different from each other and are hydrogen atom or an alkyl group with 1 to 4 carbon atoms, a hydroxyalkyl group with 1 to 3 carbon atoms or cyclic or noncyclic amino group with 2 to 6 carbon atoms, or $X^2$ and $X^3$ when taken together represent =O group or the group having the formula: —O(CH$_2$)$_b$O—, wherein b is 2 to 4, a group represented by the formula:

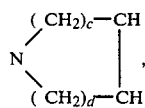

wherein c and d are the same or different from each other and are 1 to 4, a group represented by the formula:

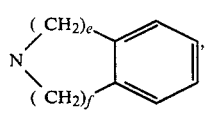

wherein e and f are the same or different from each other and are 1 to 4, or a group represented by the formula:

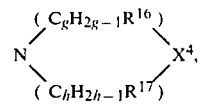

wherein g and h are the same or different from each other and are 1 to 4, $R^{16}$ and $R^{17}$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group with 1 to 3 carbon atoms, a phenyl group represented by the formula:

wherein $R^{19}$ is hydrogen atom or trifluorometyl group, or a group represented by the formula:

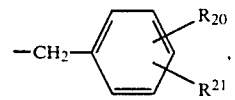

wherein $R^{20}$ and $R^{21}$ are hydrogen atoms or when taken together represent the group having the formula: —OCH$_2$O—, or a pharmaceutically acceptable salt of the rifamycin compound of formula (I) formed with a base or an acid.

2. The rifamycin compound or salt thereof of claim 1, wherein $R^1$ is acetyl group in the formula (I).

3. The rifamycin compound or salt thereof of claim 1, wherein $R^1$ is hydrogen atom in the formula (I).

4. The rifamycin compound or salt thereof of claim 1, 2, or 3, wherein $R^2$ is hydrogen atom in the formula (I).

5. The rifamycin compound or salt thereof of claim 1, 2 or 3, wherein $R^2$ is hydroxyl group in the formula (I).

6. The rifamycin compound or salt thereof of claim 1, 2, or 4, wherein $R^1$ is acetyl group and $R^2$ is hydrogen atom in the formula (I).

7. The rifamycin compound or salt thereof of claim 1, 3 or 4, wherein both $R^1$ and $R^2$ are hydrogen atoms in the formula (I).

8. The rifamycin compound or salt thereof of claim 1, wherein A is a group represented by the formula:

wherein $R^3$ is an alkyl group with 1 to 5 carbon atoms or an alkoxyalkyl group with 2 to 6 carbon atoms and $R^4$ is an alkyl group with 1 to 5 carbon atoms, a group represented by the formula: —(CH$_2$)$_a$X$^1$, wherein a is 1 to 4 and $X^1$ is ehtynyl group, a cyano group, a group represented by the formula:

wherein $R^5$ and $R^6$ are the same or different from each other and are hydrogen atom or an alkyl group with 1 to 3 carbon atoms, a group represented by the formula: $OR^7$, wherein $R^7$ is hydrogen atom or an alkyl group W 1 to 4 carbon atoms, a group represented by the formula:

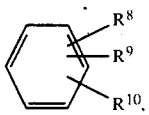

wherein $R^8$, $R^9$ and $R^{10}$ are the same or different from each other and are hydrogen atom or an alkoxy group with 1 to 3 carbon atoms, or a group represented by the formula:

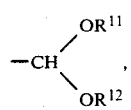

wherein $R^{11}$ and $R^{12}$ are the same or different from each other and are an alkyl group with 1 to 3 carbon atoms; a cycloalkyl group with 3 to 8 carbon atoms, a group represented by the formula:

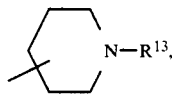

wherein $R^{13}$ is hydrogen atom or an alkyl group with 1 to 3 carbon atoms, or a group represented by the formula: $-CH_2(CHOH)_4CH_2OH$; a group represented by the formula:

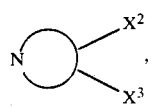

wherein

is a 3 to 10 membered cyclic amino group with 2 to 9 carbon atoms, $X^2$ is hydrogen atom or an alkyl group with 1 to 4 carbon atoms and $X^3$ is hydrogen atom, an alkyl group with 1 to 3 carbon atoms, hydroxyl group, a group represented by the formula:

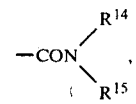

wherein $R^{14}$ and $R^{15}$ are the same or different from each other and are hydrogen atom or an alkyl group with 1 to 4 carbon atoms, an hydroxyalkyl group with 1 to 3 carbon atoms or cyclic or noncyclic amino group with 2 to 6 carbon atoms, or $X^2$ and $X^3$ when taken together represent $=O$ group or the group having the formula: $-O(CH_2)_bO-$, wherein b is 2 to 4, a group represented by the formula:

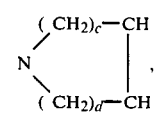

wherein c and d are the same or different from each other and are 1 to 4, a group represented by the formula:

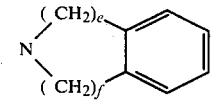

wherein e and f are the same or different from each other and are 1 to 4, or a group represented by the formula:

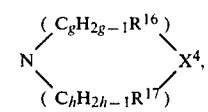

wherein g and h are the same or different from each other and are 1 to 4, $R^{16}$ and $R^{17}$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group with 1 to 3 carbon atoms, a phenyl group represented by the formula:

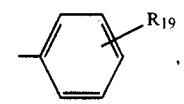

wherein $R^{19}$ is hydrogen atom or trifluoromethyl group or a group represented by the formula:

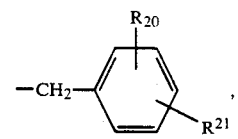

wherein $R^{20}$ and $R^{21}$ are hydrogen atoms or when taken togehter represent the group having the formula: $-OCH_2O-$ in the formula (I).

9. The rifamycin compound or salt thereof of claim 1, wherein A is a group represented by the formula:

wherein $R^3$ is an alkyl group with 1 to 5 carbon atoms or an alkoxyalkyl group with 2 to 6 carbon atoms and $R^4$ is an alkyl group with 1 to 5 carbon atoms, a group represented by the formula $-(CH_2)_aX^1$, wherein a is 1 to 4 and $X^1$ is ethynyl group, cyano group, a group represented by the formula:

wherein $R^5$ and $R^6$ are the same or different from each other and are hydrogen atom or an alkyl group with 1 to 3 carbon atoms, a group represented by the formula: $OR^7$, wherein $R^7$ is hydrogen atom or a alkyl group with 1 to 4 carbon atoms, a group represented by the formula:

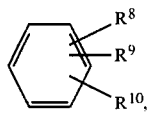

wherein $R^8$, $R^9$ and $R^{10}$ are the same or different from each other and are hydrogen atom or an alkoxy group with 1 to 3 carbon atoms, or a group represented by the formula:

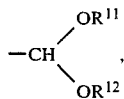

wheren $R^{11}$ and $R^{12}$ are the same or different from each other and are an alkyl group with 1 to 3 carbon atoms; a cycloalkyl group with 3 to 8 carbon atoms, a group represented by the formula:

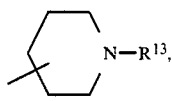

wherein $R^{13}$ is hydrogen atom or an alkyl group with 1 to 3 carbon atoms, or a group rerpresented by the formula: $-CH_2(CHOH)_4CH_2OH$ in the formula (I).

10. The rifamycin compound or salt thereof of claim 1, wherein A is a group represented by the formula:

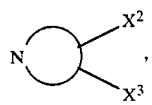

wherein

is a 3 to 10 membered cyclic amino group with 2 to 9 carbon atoms, $X^2$ is hydrogen atom or an alkyl group with 1 to 4 carbon atoms and $X^3$ is hydrogen atom, an alkyl group with 1 to 3 carbon atoms, hydroxyl group, a group represented by the formula:

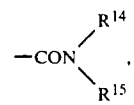

wherein $R^{14}$ and $R^{15}$ are the same or different from each other and are hydrogen atom or an alkyl group with 1 to 4 carbon atoms, a hydroxylalkyl group with 1 to 3 carbon atoms or cyclic or noncyclic amino group with 2 to 6 carbon atoms, or $X^2$ and $X^3$ when taken together represent=O group or the group having the formula: $-O(CH_2)_bO-$, wherein b is 2 to 4 in the formula (I).

11. The rifamycin compound or salt thereof of claim 1, wherein A is a group represented by the formula:

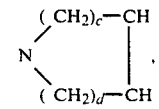

wherein c and d are the same or different from each other and are 1 to 4, or a group represented by the formula:

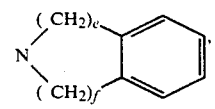

wherein e and f are the same or different from each other and are 1 to 4 in the formula (I).

12. The rifamycin compound or salt thereof of claim 1, wherein A is a group represented by the formula:

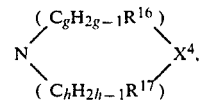

wherein g and h are the same or different from each other and are 1 to 4, $R^{16}$ and $R^{17}$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group with 1 to 3 carbon atoms, a phenyl group represented by the formula:

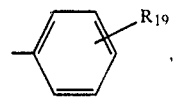

wherein R¹⁹ is hydrogen atom or trifluoromethyl group, or a group represented by the formula:

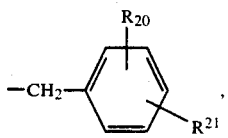

wherein $R^{20}$ and $R^{21}$ are hydrogen atom when taken together represent the group having the formula: —OCH₂O— in the formula (I).

13. The rifamycin compound or salt thereof of claim 1, wherein $R^1$ is acetyl group, $R^2$ is hydrogen atom, $R^3$ is methyl group and $R^4$ is ethyl group in the formula (I).

14. The rifamycin compound or salt thereof of claim 1, wherein $R^1$ is acetyl group, $R^2$ is hydrogen atom and both $R^3$ and $R^4$ are ethyl groups in the formula (I).

15. The rifamycin compound or salt thereof of claim 1, wherein $R^1$ is acetyl group, $R^2$ is hydrogen atom and both $R^3$ and $R^4$ are propyl groups in the formula (I).

16. The rifamycin compound or salt thereof of claim 1, wherein $R^1$ is acetyl group, $R^2$ is hydrogen atom and both $R^3$ and $R^4$ are ethoxyethyl groups in the formula (I).

17. The rifamycin compound or salt thereof of claim 1, wherein $R^1$ is acetyl group, $R^2$ is hydrogen atom, $R^3$ is methyl group and $R^4$ is 2,2-dimethoxyehtyl group in the formula (I).

18. The rifamycin compound or salt thereof of claim 1, wherein $R^1$ is acetyl group, $R^2$ is hydrogen atom and A is a group represented by the formula:

in the formula (I).

19. The rifamycin compound or salt thereof of claim 1, wherein $R^1$ is acetyl group, $R^2$ is hydrogen atom and A is a group represented by the formula:

in the formula (I).

20. The rifamycin compound or salt thereof of claim 1, wherein $R^1$ is acetyl group, $R^2$ is hydrogen atom and A is a group represented by the formula:

in the formula (I).

21. The rifamycin compound or salt thereof of claim 1, wherein $R^1$ is acetyl group, $R^2$ is hydrogen atom and A is a group represented by the formula:

in the formula (I).

22. The rifamycin compound or salt thereof of claim 1, wherein $R^1$ is acetyl group, $R^2$ is hydrogen atom and A is a group represented by the formula:

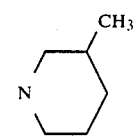

in the formula (I).

23. The rifamycin compound or salt thereof of claim 1, wherein $R^1$ is acetyl group, $R^2$ is hydrogen atom and A is a group represented by the formula:

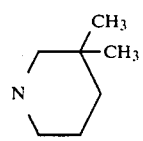

in the formula (I).

24. The rifamycin compound or salt thereof of claim 1, wherein $R^1$ is hydrogen atom, $R^2$ is hydrogen atom and A is a group represented by the formula:

in the formula (I).

25. A process for preparing a rifamycin compound having the formula (I):

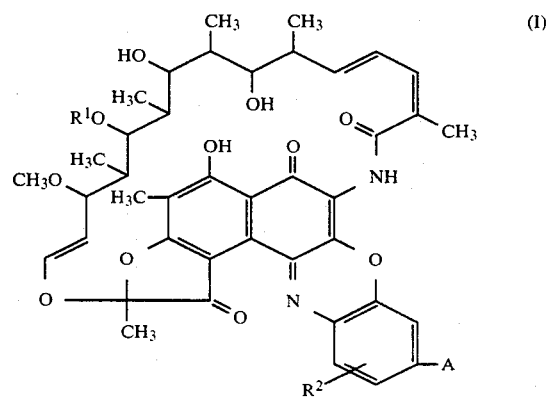

wherein $R^1$ is hydrogen atom or acetyl group $R^2$ is hydrogen atom or hydroxyl group; A is a group represented by the formula:

wherein $R^3$ is an alkyl group with 1 to 5 carbon atoms or an alkoxyalkyl group with 2 to 6 carbon atoms and $R^4$ is an alkyl group with 1 to 5 carbon atoms, a group represented by the formula: $-(CH_2)_aX^1$, wherein a is 1 to 4 and $X^1$ is ethynyl group, cyano group, a group having the formula:

wherein $R^5$ and $R^6$ are the same or different from each other and are hydrogen atom or an alkyl group with 1 to 3 carbon atoms, a group represented by the formula: $OR^7$, wherein $R^7$ is hydrogen atom an alkyl group with 1 to 4 carbon atoms, a group represented by the formula:

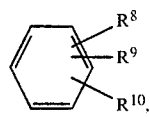

wherein $R^8$, $R^9$ and $R^{10}$ are the same or different from each other and are hydrogen atom or an alkoxy group with 1 to 3 carbon atoms, or a group represented by the formula:

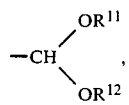

wherein $R^{11}$ and $R^{12}$ are the same or different from each other and are an alkyl group with 1 to 3 carbon atoms; a cycloalkyl group with 3 to 8 carbon atoms, a group represented by the formula:

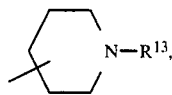

wherein $R^{13}$ is hydrogen atom or an alkyl group with 1 to 3 carbon atoms, or group represented by the formula: $-CH_2(CHOH)_4CH_2OH$; a group represented by the formula:

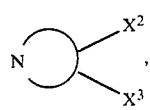

wherein

is a 3 to 10 membered cyclic amino group with 2 to 9 carbon atoms, $X^2$ is hydrogen atom or an alkyl group with 1 to 4 carbon atoms and $X^3$ is hydrogen atom, an alkyl group with 1 to 3 carbon atoms, hydroxyl group, a group represented by the formula:

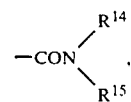

wherein $R^{14}$ and $R^{15}$ are the same or different from each other and are hydrogen atom or an alkyl group with 1 to 4 carbon atoms, a hydroxyalkyl group with 1 to 3 carbon atoms or cyclic or noncyclic amino group with 2 to 6 carbon atoms, or $X^2$ and $X^3$ when taken together represent O=group or the group represented by the formula: $-O(CH_2)_bO-$, wherein b is 2 to 4, a group represented by the formula:

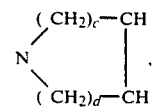

wherein c and d are the same or different from each other and are 1 to 4, a group represented by the formula:

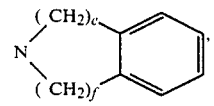

wherein e and f are the same or different from each other and are 1 to 4, or a group represented by the formula:

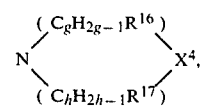

wherein g and h are the same or different from each other and are 1 to 4, $R^{16}$ and $R^{17}$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group with 1 to 3 carbon atoms, a phenyl group represented by the formula:

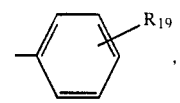

wherein $R^{19}$ is hydrogen atom or trifluoromethyl group, or a group represented by the formula:

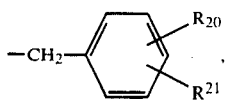

wherein $R^{20}$ and $R^{21}$ are hydrogen atoms or when taken together represent the group having the formula: —OCH$_2$O—, or a pharmaceutically acceptable salt of the rifamycin compound of formula (I) formed with a base or an acid, which comprises reacting a rifamycin derivative having the formula (II):

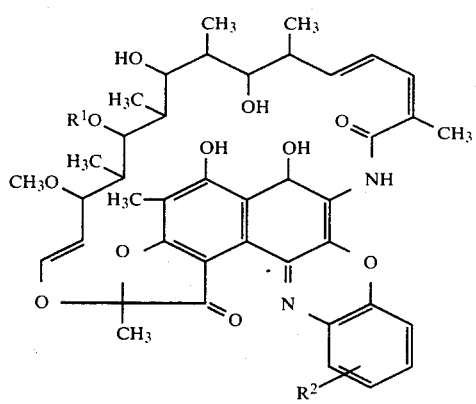

wherein $R^1$ and $R^2$ are as defined above, with an amine having the formula: AH, wherein A is as defined above.

26. The process of claim 25, wherein the rifamycin compound having the formula (II) is reacted with the amine having the general formula: AH in the presence of an oxidizing agent.

27. The process of claim 25, or 26, wherein the oxidizing agent is manganese dioxide.

28. A process for preparing a rifamycin compound having the formula (I), wherein $R^1$ is hydrogen atom and $R^2$ and A are as defined above, which comprises reacting a compound having the formula (II) wherein $R^1$ is acetyl and $R^2$ is as defined above, with an amine having the formula AH wherein A is as defined above, to prepare a compound having the formula (I) wherein $R^1$ is acetyl and $R^2$ and A are as defined above, and then hydrolyzing the obtained compound to give a rifamycin compound having the formula (I), wherein $R^1$ is hydrogen atom, and $R^2$ and A are as defined above.

29. The process of claim 28, wherein an agent employed for hydrolysis is alkali metal hydroxide.

30. An antibacterial pharmaceutical composition which comprises a pharmaceutical carrier, and a rifamycin compound having the formula (I):

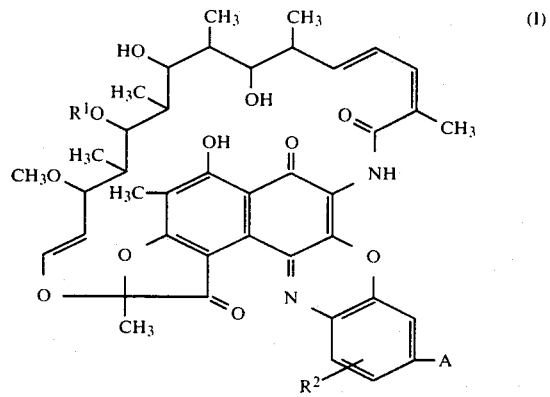

wherein $R^1$ is hydrogen atom or acetyl group: $R^2$ is hydrogen atom or hydroxyl group; A is a group represented by the formula:

wherein $R^3$ is an alkyl group with 1 to 5 carbon atoms or an alkoxyalkyl group with 2 to 6 carbon atoms and $R^4$ is an alkyl group with 1 to 5 carbon atoms, a group represented by the formula: —(CH$_2$)$_a$X$^1$, wherein a is 1 to 4 and $X^1$ is ethynyl group, cyano group, a group having the formula:

wherein $R^5$ and $R^6$ are the same or different from each other and are hydrogen atom or an alkyl group with 1 to 3 carbon atoms, a group represented by the formula: OR$^7$, wherein $R^7$ is hydrogen atom or an alkyl group with 1 to 4 carbon atoms, a group represented by the formula:

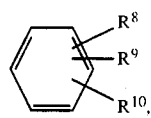

wherein $R^8$, $R^9$ and $R^{10}$ are the same or different from each other and are hydrogen atom or an alkoxy group with 1 to 3 carbon atoms, or a group represented by the formula:

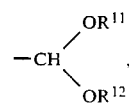

wherein $R^{11}$ and $R^{12}$ are the same or different from each other and are an alkyl group with 1 to 3 carbon atoms; a cycloalkyl group with 3 to 8 carbon atoms, a group represented by the formula:

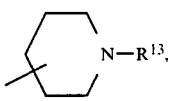

wherein $R^{13}$ is hydrogen atom or an alkyl group with 1 to 3 carbon atoms, or a group represented by the formula: $-CH_2(CHOH)_4CH_2OH$; a group represented by the formula:

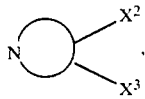

wherein

is a 3 to 10 memebered cyclic amino group with 2 to 9 carbon atoms, $X^2$ is hydrogen atom or an alkyl group with 1 to 4 carbon atoms and $X^3$ is hydrogen atom, an alkyl group having 1 to 3 carbon atoms, hydroxyl group, a group represented by the formula:

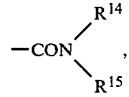

wherein $R^{14}$ and $R^{15}$ are the same or different from each other and are hydrogen atom or an alkyl group with 1 to 4 carbon atoms, a hydroxyalkyl group with 1 to 3 carbon atoms or cyclic or noncyclic amino group with 2 to 6 carbon atoms, or $X^2$ and $X^3$ when taken together represent =O group or the group represented by the formula: $-O(CH_2)_bO-$, wherein b is 2 to 4, a group represented by the formula:

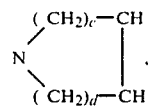

wherein c and d are the same or different from each other and are 1 to 4, a group represented by the formula:

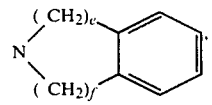

wherein e and f are the same or different from each other and are 1 to 4, or a group represented by the formula:

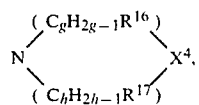

wherein g and h are the same or different from each other and are 1 to 4, $R^{16}$ and $R^{17}$ are the same or different from each other and are hydrogen atom or an alkyl group with 1 to 3 carbon atoms and $X^4$ is oxygen atom, sulfur atom or a group represented by the formula: $NR^{18}$, wherein $R^{18}$ is hydrogen atom, an alkyl group with 1 to 3 carbon atoms, a phenyl group represented by the formula:

wherein $R^{19}$ is hydrogen atom or trifluoromethyl group, or a group represented by the formula:

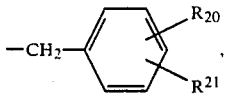

wherein $R^{20}$ and $R^{21}$ are hydrogen atoms or when taken together represent the group having the formula: $-OCH_2-$, or a pharmaceutically acceptable salt of the rifamycin compound of formula (I) formed with a base or an acid as an effective component, wherein the ratio of the rifamycin compound (I) to the pharmaceutical carrier is 0.2 to 100% by weight.

* * * * *

UNITED STATES PATENT AND TRADEMARK OFFICE
CERTIFICATE OF CORRECTION

PATENT NO. : 4,690,919
DATED : September 1, 1987
INVENTOR(S) : YAMANE et al

It is certified that error appears in the above-identified patent and that said Letters Patent is hereby corrected as shown below:

Column 2, line 60 to 64,

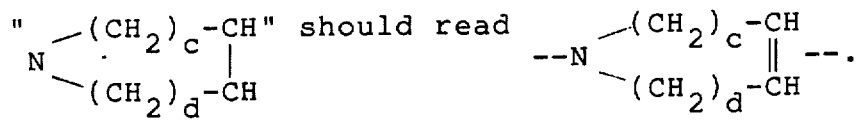

Column 3, line 22, "$R^7$" should read --$R^{17}$--;
        line 35, "$R_{19}$" should read --$R^{19}$--;
        line 45, "$R_{20}$" should read --$R^{20}$--;
        line 53, "OCH2O" should read --$OCH_2O$--.

Column 4, line 32, "$-CH_2)_a X^1$" should read -- $-(CH_2)_a X^1$--;
        line 65, "R12" should read --$R^{12}$--.

Column 5, lines 50 to 54,

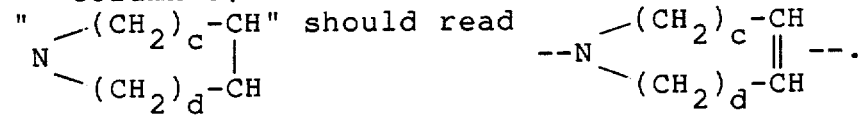

Column 6, line 20, "$R_{19}$" should read --$R^{19}$--;
        line 30, "$R_{20}$" should read --$R^{20}$--.

Table 1, derivative No. 10

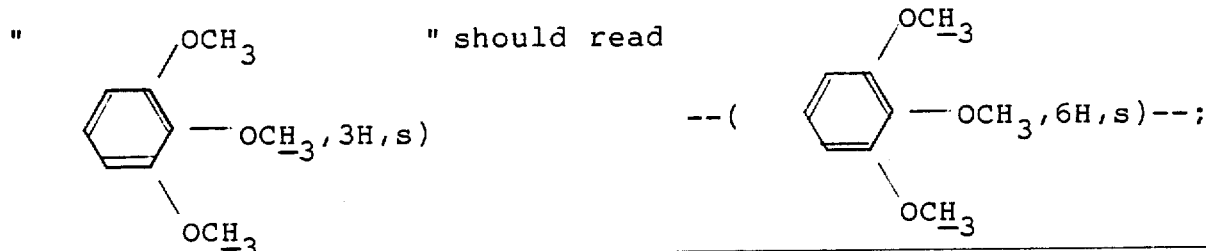

UNITED STATES PATENT AND TRADEMARK OFFICE
CERTIFICATE OF CORRECTION

PATENT NO. : 4,690,919     Page 2 of 4
DATED : September 1, 1987
INVENTOR(S) : YAMANE et al It is certified that error appears in the above-identified patent and that said Letters Patent is hereby corrected as shown below:

and also, Table 1, derivative 10,

" 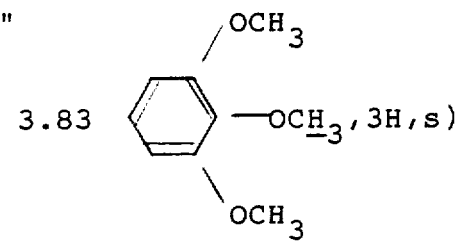 should read 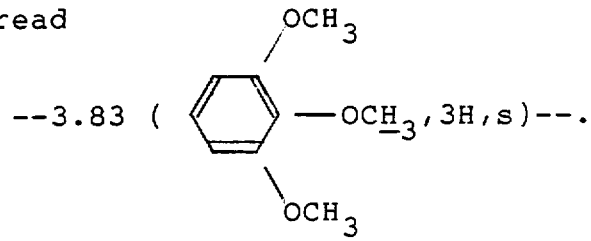

Column 23, line 8, "(Tokyo), 29, P76" should read --(Tokyo), $\underline{29}$, p76--;
        line 48, "Wister" should read --Wistar--;
        line 49, "27" should read --270--.

Column 25, line 12, "Acta, 56" should read --Acta, $\underline{56}$--;
        line 39, "$\delta$max" should read --$\lambda$max--;
        line 53, "maganese" should read --manganese--;
        line 58, "Walpgel" should read --Wakogel--.

Column 26, line 9, "$\delta$max" should read --$\lambda$max--;
        line 56, "$CDCL_3$" should read --$CDCl_3$--.

Column 27, line 6, "N-methylpropagylamine" should read --N-methylpropargylamine--.

Column 28, line 50, "$\nu$ -1" should read --$\nu$ $cm^{-1}$--;
        line 64, "$E^{1\%}_{1cm}$ 9" should read --$E^{1\%}_{1cm}$--.

Column 30, line 3, "$E^{1\%}_{1}$" should read --$E^{1\%}_{1cm}$--;
        line 33, "max.n" should read --max.nm--.

Column 35, line 43, "1.74 ml or" should read --1.74 ml of--.

UNITED STATES PATENT AND TRADEMARK OFFICE
CERTIFICATE OF CORRECTION

PATENT NO. : 4,690,919

DATED : September 1, 1987

INVENTOR(S) : YAMANE et al

It is certified that error appears in the above-identified patent and that said Letters Patent is hereby corrected as shown below:

Column 33, line 13, "No. 28" should read --No. 29--.

Column 38, lines 31 and 32, "$X^\ell$" should read --$X^1$--.

Column 39, lines 50 to 54, 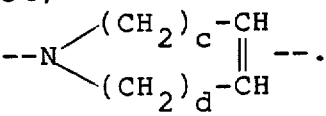 .

Column 40, line 20, "$R_{19}$" should read --$R^{19}$--;
line 30, "$R_{20}$" should read --$R^{20}$--.

Column 41, line 11, "group W" should read --group with--.

Column 42, lines 16 to 20, 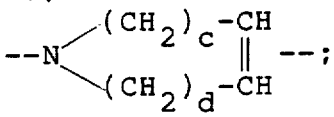 ;

line 50, "$R_{19}$" should read --$R^{19}$--;

line 60, "$R_{20}$" should read $R^{20}$--.

Column 44, line 65, 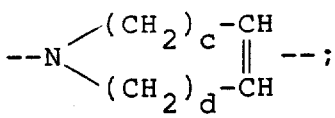 ;

line 65, "$R_{19}$" should read --$R^{19}$--.

Column 45, line 5, "$R_{20}$" should read --$R^{20}$--.

Column 48, line 24, "O=group" should read --=O group--;

UNITED STATES PATENT AND TRADEMARK OFFICE
CERTIFICATE OF CORRECTION

PATENT NO. : 4,690,919

DATED : September 1, 1987

INVENTOR(S) : YAMANE et al

Page 4 of 4

It is certified that error appears in the above-identified patent and that said Letters Patent is hereby corrected as shown below:

Column 48, line 30, $$"N\begin{matrix}(CH_2)_c-CH\\ (CH_2)_d-CH\end{matrix}" \text{ should read } --N\begin{matrix}(CH_2)_c-CH\\ \phantom{(CH_2)_d-}\|\\ (CH_2)_d-CH\end{matrix}--;$$

line 65, "$R_{19}$" should read --$R^{19}$--.

Column 49, line 5, "$R_{20}$" should read --$R^{20}$--.

Column 51, line 54, "=O group" should read --=O group--.

Column 52, line 5, $$"N\begin{matrix}(CH_2)_c-CH\\ (CH_2)_d-CH\end{matrix}" \text{ should read } --N\begin{matrix}(CH_2)_c-CH\\ \phantom{(CH_2)_d-}\|\\ (CH_2)_d-CH\end{matrix}--;$$

line 35, "$R_{19}$" should read --$R^{19}$--;

line 45, "$R_{20}$" should read --$R^{20}$--;

line 51, "-$OCH_2$-" should read -- -$OCH_2O$- --.

Signed and Sealed this

Twenty-sixth Day of July, 1988

Attest:

DONALD J. QUIGG

Attesting Officer

Commissioner of Patents and Trademarks